United States Patent [19]

Deckman et al.

[11] Patent Number: 4,891,829
[45] Date of Patent: Jan. 2, 1990

[54] METHOD AND APPARATUS FOR UTILIZING AN ELECTRO-OPTIC DETECTOR IN A MICROTOMOGRAPHY SYSTEM

[75] Inventors: Harry W. Deckman; Brian P. Flannery, both of Clinton, N.J.

[73] Assignee: Exxon Research and Engineering Company, Florham Park, N.J.

[21] Appl. No.: 932,273

[22] Filed: Nov. 19, 1986

[51] Int. Cl.$^4$ .................. G01N 23/00; G01N 23/08
[52] U.S. Cl. .......................... 378/4; 378/19; 378/901; 364/413.19
[58] Field of Search ............ 378/4, 19, 15, 20, 901; 250/370 I, 370 G, 369, 486.1; 364/414

[56] References Cited

U.S. PATENT DOCUMENTS

| | | | |
|---|---|---|---|
| 4,071,760 | 1/1978 | LeMay | 378/19 |
| 4,298,800 | 11/1981 | Goldman | 378/19 |
| 4,343,995 | 8/1982 | Klausz | 378/4 |
| 4,521,688 | 6/1985 | Yin | 250/369 |
| 4,670,840 | 6/1987 | Freundlich | 378/4 |
| 4,682,291 | 7/1987 | Reuveni | 378/901 |

Primary Examiner—Carolyn E. Fields
Assistant Examiner—Joseph A. Hynds
Attorney, Agent, or Firm—Ronald D. Hantman

[57] ABSTRACT

The present invention is an apparatus and a method for producing tomographic images of an object irradiated by a beam of collimated radiation transmitted in a plurality of rays through a set of coplanar sections of an object as viewed from a plurality of angles about a rotation axis. The apparatus includes an imaging electro-optic detector to record the transmitted radiation, wherein the electro-optic detector alters the image format, the format alteration being focused; means to determine and align the projected position of the rotation axis on the electro-optic detector; means to align the object with respect to the rotation axis; means to determine and assure spatial uniformity of detector response; means to reduce signal dependent backgrounds; means to determine the projection coefficients from the transmitted radiation with respect to one or more reference calibration exposures; and means to compute a reconstructed image of the object's attenuation coefficients.

38 Claims, 12 Drawing Sheets

ELECTRO-OPTIC X-RAY DETECTORS

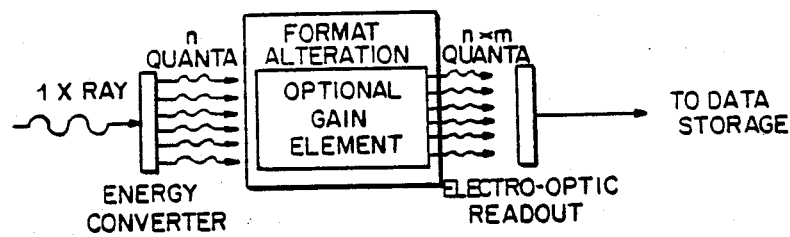

- ENERGY CONVERTERS
    - PHOSPHORS (OPTICAL AND PHOTOELECTRON)

- GAIN ELEMENTS
    - MICROCHANNEL PLATES
    - ELECTROSTATICALLY FOCUSED INTENSIFIER
    - MAGNETICALLY FOCUSED INTENSIFIER

- FORMAT ALTERATION
    - OPTICAL LENS
    - FIBEROPTIC BUNDLES
    - REDUCING IMAGE INTENSIFIER

- ELECTRO OPTIC READOUT
    - IMAGE ORTHOCON
    - VIDICON
    - SIT
    - CID
    - CCD
    - IMAGE ISOCON
    - SEC VIDICON
    - SILICON DIODE VIDICON
    - RESISTIVE ANODE

FIG.1

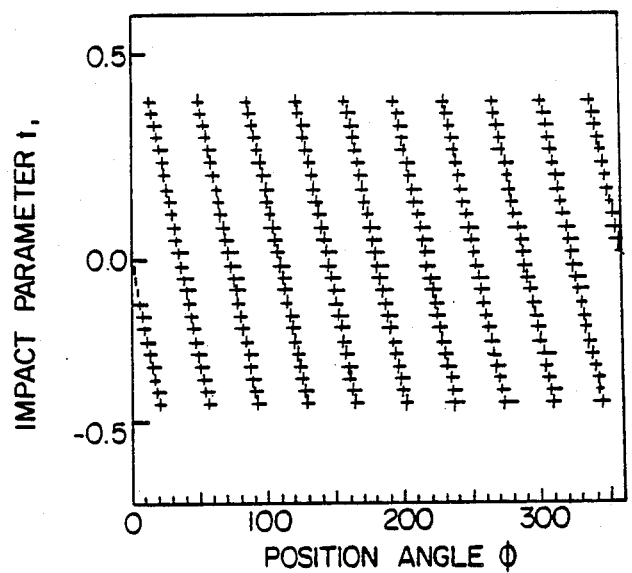
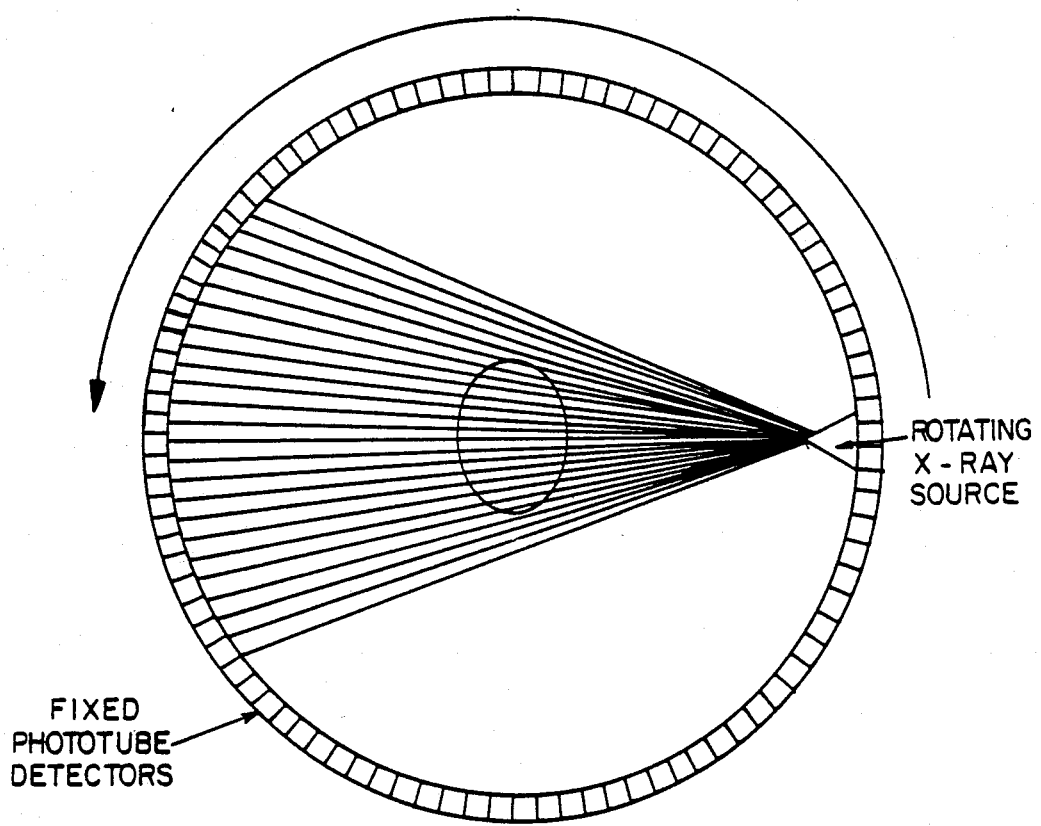
FIG. 3

1% RINGS
5% RINGS
10% RINGS
50% RINGS
F I G. 8

METHOD AND APPARATUS FOR UTILIZING AN ELECTRO-OPTIC DETECTOR IN A MICROTOMOGRAPHY SYSTEM

Computerized tomography refers to the procedures used to generate two dimensional maps of some physical quantity in a planar section of a target by measuring and analyzing the attenuation of beams of penetrating radiation passed through the target along sets of coplanar rays. As practiced, a complete apparatus must contain four elements: (1) a source of penetrating radiation, (2) detectors that measure the transmitted intensity of the radiation after passage through the target, and that can be calibrated to give the unattenuated intensity of radiation in the absence of the target, (3) a computational device to store and process the attenuation measurements, converting them into a digital map of attenuation coefficients in the observed plane of the target, and (4) a device to display the resultant image.

Tomography can be practiced in many ways, but the broadest commercial usage is in medical radiology to provide diagnostic maps of bone and tissue structure in human patients (W. Swindell and H. H. Barett, "Computerized Tomography: Taking Sectional X-Rays", Physics Today, pp. 32–41, 1977; C. C. Jaffe, "Medical Imaging", American Scientist, 70, 576 (1982); and P. Alexander, "Array Processors in Medical Imaging", Computer, 16, (1983). Medical CT uses broad band bremsstrahlung radiation from X-ray tubes to produce penetrating radiation that is measured, typically, by scintillation crystals and photo-tubes. Measurements are stored in a programmable digital computer and analyzed using a method generically referred to as convolution (or filtered) back projection (referred to hereafter as FBP). The density map derived from the analysis is displayed on a cathode ray tube as a two dimensional cross sectional image containing approximately 250×250 elements or pixels, with a resolution of about 1 millimeter, and 1% accuracy in determination of X-ray attenuation coefficient. Medical procedures typically produce scans in only a limited number of adjacent body planes, typically one to twenty. However, special purpose tomography probes have been built using different types of ionizing radiation, such as gamma rays and electrons.

An object of the present invention is to provide a method for using an imaging electro-optic detector in acquiring tomographic data. By using an electro-optic detector instead of conventional scintillation detectors spatial resolution and physical scale in reconstructed images can be significantly improved. Spatial resolution attainable using electro-optic detectors can be as small as 0.5 microns which is 100–1,000 times better than that achieved with scintillation detectors in conventional medical CT. Physical scale in the reconstructed image is increased by acquiring data in muliple stacked planes simultaneously. The number of resolution elements per plane is comparable to or significantly greater than that for conventional medical CT. Increasing the physical scale in this manner permits reconstruction of an object on a three dimensional network of points. The amount of data acquired and processed to reconstruct an object on a three dimensional grid containing $N^3$ points is much greater than in medical CT. Since the number of data points, N, acquired in a line across the image can be greater than 500, it is important to utilize data inversion techniques requiring $N^2$ rather than $N^3$ operations to reconstruct an image. When an object is reconstructed on a three dimensional network of points, the methods described herein can be though of as part of the operation of a three dimensional X-ray microscope.

SUMMARY OF THE INVENTION

The present invention is an apparatus and a method for producing tomographic images of an object irradiated by a beam of collimated radiation transmitted in a plurality of rays through a set of coplanar sections of an object as viewed from a plurality of angles about a rotation axis. The apparatus includes an imaging electro-optic detector to record the transmitted radiation, wherein the electro-optic detector alters the image format, the format alteration being focused; means to determine and align the projected position of the rotation axis on the electro-optic detector; means to align the object with respect to the rotation axis; means to determine and assure spatial uniformity of detector response; means to reduce signal dependent backgrounds; means to determine the attenuation (projection coefficients) from the transmitted radition with respect to one or more reference calibration exposures; and means to compute a reconstructed image of the object's attenuation coefficients.

BRIEF DESCRIPTION OF THE DRAWINGS

FIG. 1—Schematic diagram showing the generic components of an x-ray electro-optic detector. Specific components are enumerated for the energy convertor, optional gain element, format alteration and electro-optic readout.

FIG. 3 is a schematic showing observational paths in a typical medical CT scanner using the "fan beam" observational mode. Discrete observational paths occur at points $(t_1, \phi)$ as shown in the upper pannel.

FIG. 8—Mathematical simulation of ring artifacts which result from uncorrected variations in pixel to pixel detector response. Successive reconstructions of a simulated sandstone target are shown with 1, 5, 10 and 50% modulations added to the projection data.

DESCRIPTION OF THE PREFERRED EMBODIMENT

Figure 2:
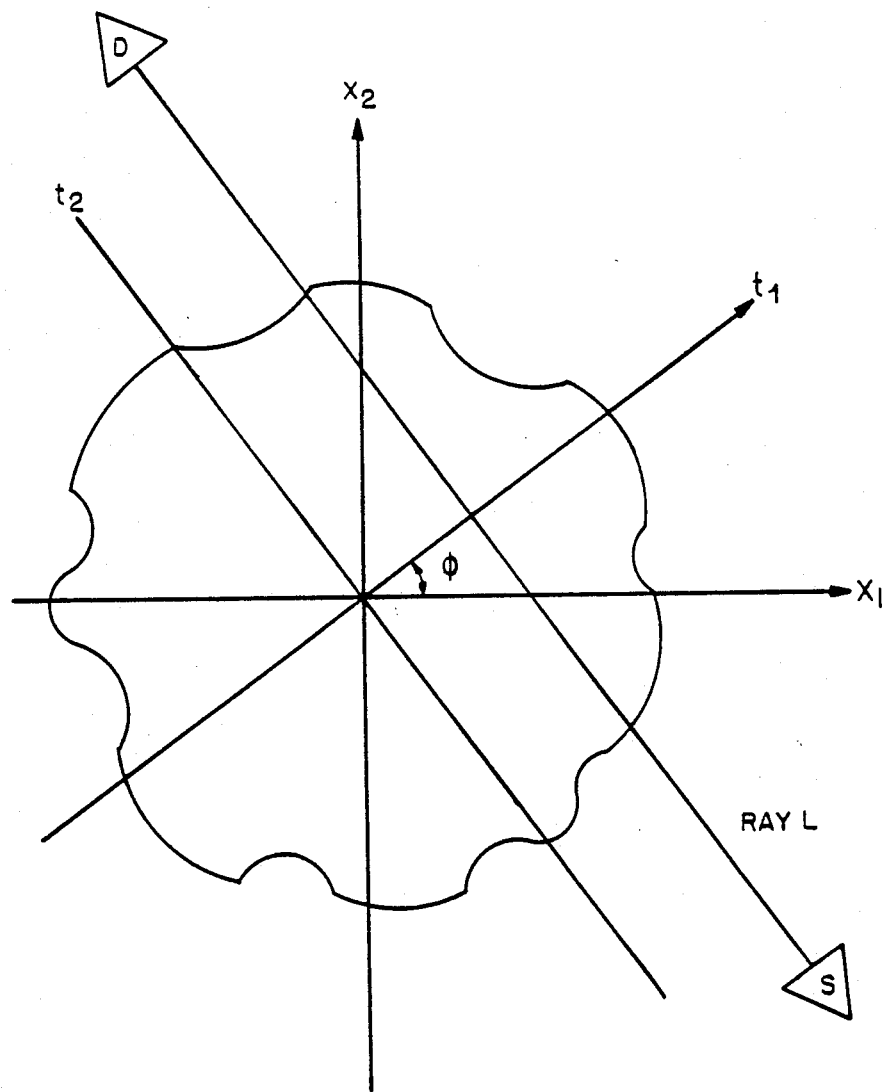
FIG. 2 shows the geometry defining a path through the observed plane of a target. The path L between the source, S, and detector, D, is defined by its impact parameter $t_1$ and angle $\phi$ with respect to a set of fixed cartesian axes $(x_1, x_2)$ in the target.

This invention is broadly a method for using a new type of detector for computerized tomography. The detector can be used in a mode which increases spatial resolution in reconstructed images, below 10 microns. A particular form of the detector can be used to acquire data in multiple stacked planes, allowing the internal structure of a sample to be reconstructed on a three dimensional network of points. In this mode the device described herein functions as a three dimensional x-ray microscope.

The detector is usable with any form of radiation which can be converted within the detector to more easily handle quanta which are used to form an image on a recording device within the detector. In general, radiations which fulfill this requirement are ionizing radiations such as X-rays, gamma rays, neutrons and ultraviolet light. It should be noted that fluorescent conversion processes for visible light in which no ionized state is formed are included within the definition of radiations which can be used with the detector. The present invention will be illustrated using X-rays as the radiation detected, although any of the other allowable radiation forms can be used.

Detectors utilized in the present invention form a distinct subset of the broad class of electro-optic radiation detectors. Electro-optic radiation detectors can be broadly defined as position sensitive detectors which utilize components developed for the amplification and recording of optical images. Because of the imaging characteristics of this class of detectors, significantly higher spatial resolutions can be obtained than are possible with scintillation detectors used in conventional tomographic devices.

The generic detector, as depicted in FIG. 1, consists of four elements: an energy converter, an optional gain element, a device to magnify or demagnify the image (i.e., an image format altering device) and a readout device. The function of the energy converter is to distribute the energy of the X-ray photon amongst numerous, more easily handled quanta. Typically, it is a phosphor screen which produces visible light. In some cases, it may be an electron emitting photocathode. Often, the quanta produced in the converter are still too few in number to be effectively recorded in the readout device; consequently, a gain element may be interposed. Typical gain elements are magnetic or electrostatically focused image intensifiers or microchannel plates. The format of the output from the gain element (or phosphor) must usually be altered before it is recorded with an imaging readout device. Format alteration is necessary because the image from the gain element or phosphor usually differs in size from the readout device. Hence it is usually necessary to couple the two via magnifying or reducing mechanisms. Magnification or demagnification of the image can be accomplished with either electron or light optics. Light optic format alterations can be accompanied using either lens or fiber optic coupling. With electron optics, format alterations can be obtained from electrostatic focusing in an image intensifier. Readout devices are the most diverse class of element in electro-optic detectors. They range from a bewildering assortment of vacuum tubes, to solid state detector arrays, to resistive anode devices, several of which are listed in FIG. 1.

In recent years, solid state charge coupled devices (CCD) have evolved to become the preeminent electro-optical sensor technology and in a preferred embodiment are used as readout devices. The most important aspect of CCD sensors for optical image detection is that they exhibit a readout and dark noise which is at least an order of magnitude lower than vidicons, isocons, orthocons and other electro-optic sensors. Commercially available CCD sensors have a readout noise of less than 50 electrons/pixel and a dark noise of less than 5 electrons/minute-pixel when operated at temperatures below $-75°$ C. These low noise figures result in substantial improvements in detective quantum efficiency of electro-optic x-ray detectors constructed with CCD sensors. CCD sensors also exhibit the largest dynamic range (saturation signal/r.m.s. readout noise) of all electro-optic sensors. Saturation signals on many CCD sensors approach $\sim 10^6$ electrons/pixel yielding a dynamic range for signal detection of $\sim 10^5$. On some chips a limitation exists when the saturation level is approached, due to the lack of an ability to locally saturate pixels. For signal levels below saturation, CCD sensors exhibit linearity of response with signal intensity which is independent of counting rate. Lack of any count rate limitations make CCD sensors suitable as area detectors for intense synchrotron radiation. The lack of count rate limitations, is due to integration of charge produced from separation of electron-hole pairs generated by the signal in each pixel until the device is read-out. Accumulated charge is read out from CCD sensors by passing charge from pixel to pixel in a bucket brigade fashion to an onboard charge sensitive preamplifier. Noise in readout of the onboard preamplifier is substantially reduced through use of a double correlated sampling technique, which cannot be used with other electro-optical sensor technologies. Readout rate is limited by the requirement that the efficiency of transferring charge from pixel to pixel be greater than 99.99% (99.999% charge transfer efficiencies can be achieved on some chips). For most chips readout rates faster than 1–10 microseconds/pixel degrade the charge transfer efficiency. Since defect free CCD sensors containing $5\times 10^5$ pixels have been manufactured and chips containing $5\times 10^7$ pixels are being developed, readout time for CCD chips can vary from 0.1-10 sec. These readout times are too slow for most time resolved x-ray experiments, however, CCD detectors can operate in a time resolved mode which shifts either all columns or rows of pixels over one position without reading the entire device. In this mode it is possible to use a CCD sensor to record changes in x-ray signals with a temporal resolution of microseconds.

Only a few of the tremendous number of configurations for the different converter, gain, and readout elements available are suitable for use as a quantative detector needed in tomography, even though most configurations can produce a visually pleasing image. Limitations on the number of electro-optic detector configurations which can be used in tomography stem from the following detector attributes:

(1) Quantum detection efficiency, (2) signal dependent backgrounds in the recorded image, (3) useful dynamic range of the detector, (4) spatial uniformity of response (quantum uniformity), (5) positional linearity (geometric linearity). These performance criteria must have a particular range of values to make a two dimensional x-ray detector suitable for a tomographic system. Applicable ranges of these performance criteria can be determined from image quality and signal to noise considerations. These considerations also restrict the way in which electro-optic detectors can be used to gather data for computerized tomography. It will be shown that these considerations require that:

(a) Radiation used in the tomography system be collimated (b) The optical image created at the energy converter plate must be sharply focused on the readout device (c) The rotation axis of the sample must be carefully aligned with respect to the pixels of the detector (d) Pixel to pixel variations in the electro-optic detector response must be accurately correctable (e) A signal dependent background which is intrinsic to electro-optic detector must be minimized (f) Reference calibration exposures must be used to accurately compensate for electro-optic detector attributes.

To determine the nature of these limitations we examine the protocols for data acquisition, signal to noise considerations and inversion methods.

PROTOCOL FOR DATA ACQUISITION

To generate accurate tomographic images, sufficiently noise-free data must be obtained along a sufficient number of independent coplanar paths through the target (L. A. Shepp and B. F. Logan, "The Fourier Reconstruction of a Head Section", IEEE Trans. Nucl. Sci., Vol. NS-21, pp. 21–43, 1974. Observational paths can be labeled according to their view angle $\phi$ and impact parameter $t_1$, with respect to coordinates fixed in the target, as shown in FIG. 2. In medical tomography measurements are typically obtained with a fixed set of detectors located along a ring surrounding the patient, as shown in FIG. 3. The X-ray source rotates about the ring, illuminating a series of detectors opposite the source with a collimated fan beam of radiation. The opening angle of the collimated X-ray beam is broad enough so that the fan of paths from source to detector completely encompasses the target. For accurate reconstruction of the entire target, the range of impact parameters must span the diameter of the target and the angular rotations must span at least one half of a complete rotation. We refer to the mode of operation shown in FIG. 3 as fan beam collimation.

Figure 4:
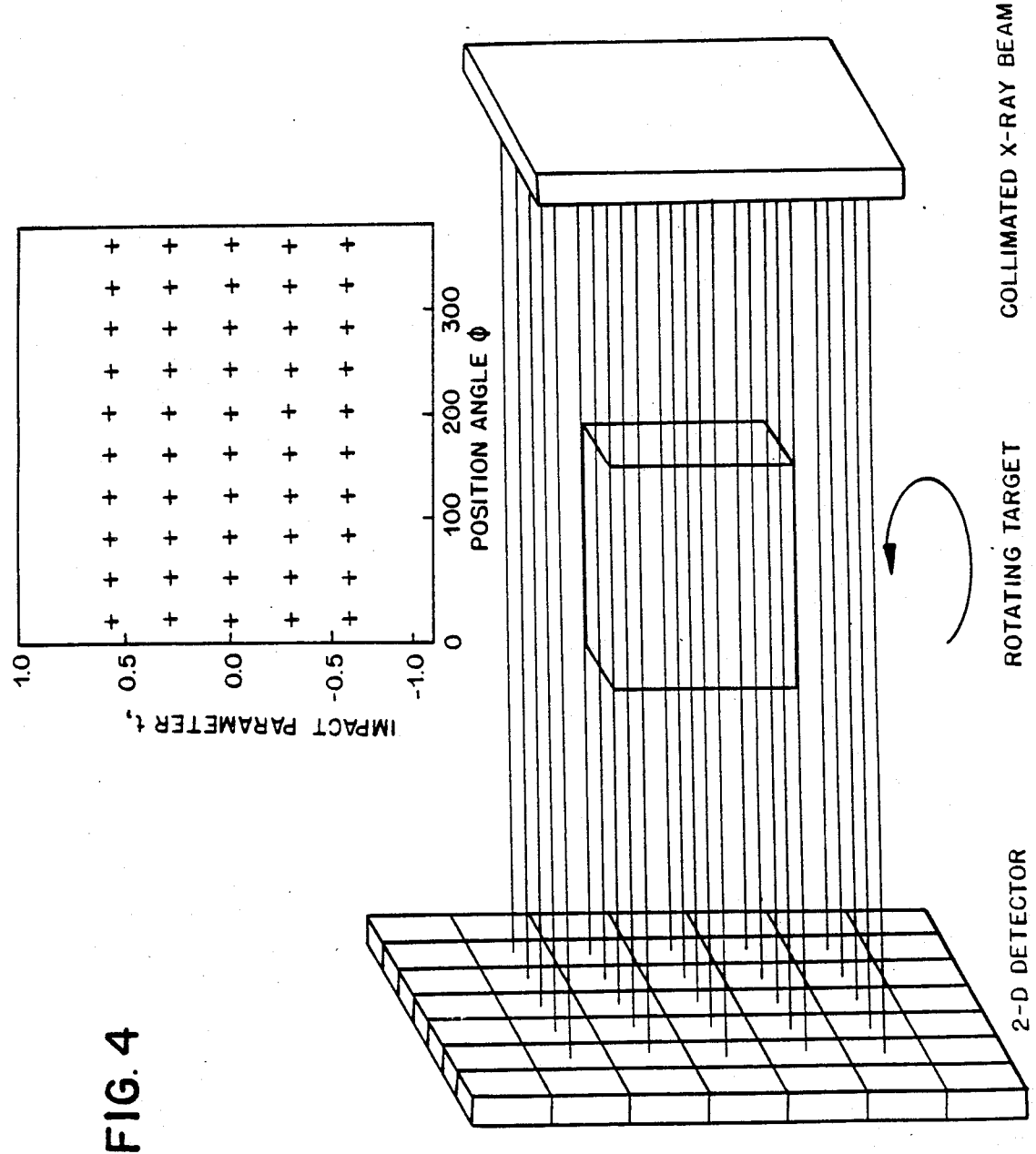
FIG. 4 is a schematic showing observational paths in a scanner using the "parallel beam" observational mode. Here a parallel, collimated beam of radiation irradiates the target in multiple stacked planes and multiple impact parameters simultaneously. The target is rotated for observations at different view angles $\phi$. Discrete observational paths in one of the planes occur at points $(t_1, \phi)$ as shown in the upper pannel.

Another mode of operation for a tomographic scanner is shown in FIG. 4. Collimated X-rays, or other penetrating radiation, illuminate the target along two dimensional sets of plane parallel paths that are recorded by a panoramic detector. If a two dimensional imaging electro-optic detector is used, data in multiple stacked planes is measured simultaneously. Views from different angles are achieved by rotating the target (as shown in FIG. 4) or by rotating both source and detector around a stationary sample. Data taken in this geometry are said to be taken in plane parallel mode. The plane parallel mode of data acquisition is clearly preferred when high spatial resolution between 0.5 and 25 microns is selected. For high spatial resolution dta acquisition, X-ray beams can be readily collimated for the plane parallel mode shown in FIG. 4, whereas appropriate collimation for the fan beam geometry is difficult. Throughout this application, we will illustrate the use of electro-optic detectors with the plane parallel mode of data acquisition. However, the invention is also applicable to the fan beam mode of data acquisition. Also, the application will be illustrated for the case in which the sample is physically rotated.

PROJECTION MEASUREMENTS AND INVERSION METHODS

In transmission tomography the intensity of the incident ($I_0$) and detected ($I_D$) beam are related by attenuation along the path through the target. In the absence of scattering $$I_D = I_0 \exp[-\int F(t_1,t_2)dt_2] \qquad \text{Eq. 1}$$

where $F(t_1,t_2)$ is the linear attenuation coefficient in the target, and the integration over $t_2$ traverses the beam's path (see FIG. 2). The quantity actually used in tomographic analysis is the optical depth or "projection" $P(\phi,t_1)$ defined as $$P(\phi,t_1) = \ln[I_0(\phi,t_1)/I_D(\phi,t_1)]. \qquad \text{Eq. 2}$$

The apparatus makes panoramic measurements of transmitted radiation that can be used to obtain both $I_O$ and $I_D$. This is achieved through use of a suitable calibration procedure. It is an object of the present invention to define calibration procedures for electro-optic detectors so that projections can be measured with sufficient accuracy for processing by reconstruction algorithms.

The goal of tomography is to recover $F(x,y)$ from measurements of its line integral $P(\phi,t_1) = \int F dt_2$. In general, inversion methods reconstruct the attenuation coefficient $F(x,y)$ at a point as a linear weighted summation of the measured projection data $$F(x,y) = \Sigma_m \Sigma_n w(x,y;\phi_m,t_n) P(\phi_m,t_n) \qquad \text{Eq. 3}$$

where the weights $w(x,y;\phi_m,t_n)$ depend on the position in the target and the orientation of the scan. Eq. 3 indicates that the scan data can be inverted to evaluate $F(x,y)$ at any arbitrary point inside the target.

Initial reconstruction methods for medical tomography used an interative procedure (see U.S. Pat. No. 3,778,614) to recover the attenuation coefficients $F(x,y)$. Starting with an arbitrary initial trial solution, the method computationally derived values for projection data that would occur from the trial image. Differences between measured and derived projection data were used to correct the trial image successively until sufficient agreement was obtained between computed and observed projections.

Later, the far better method for convolution backprojection [also referred to as Filtered Backprojection (FBP)] was developed and applied in a tomography apparatus (L. A. Shepp and B. F. Logan, "The Fourier Reconstruction of a Head Section", IEEE Trans. Nucl. Sci., Vol. NS-21, pp. 21-43, 1974 and C. A. G. LeMay, U.S. Pat. No. 3,924,129. Filtered backprojection (FBP) has been extensively practiced for commercial tomographic reconstructions. It is directly applicable to both fan beam and plane parallel modes of data acquisition.

Another method for reconstructing utilizes Direct Fourier Inversion Methods (DFI). Its essential advantage over FBP is that the number of mathematical operations required to invert data to form an image of size $N \times N$ pixel scales as $N \times N \times N$ is FBP but only $N \times N \times \log_2(N)$ in the DFI method. For example, the DFI method inverts data 40 times faster than FBP for images containing $256 \times 256$ pixels and its relative speed advantage grows for larger images.

Figure 5:
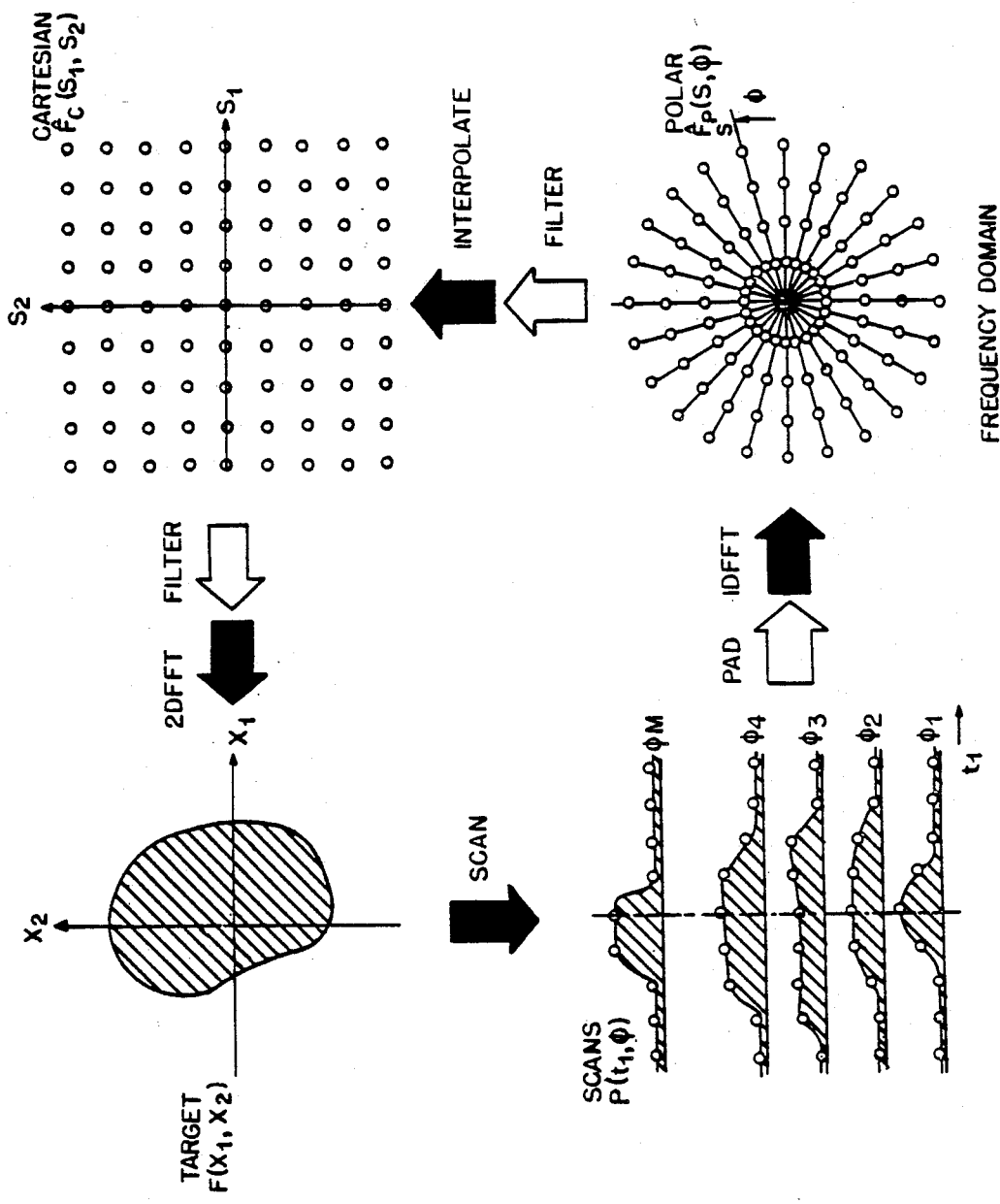
FIG. 5 is a schematic of the steps of the Direct Fourier Inversion Method showing the relation between the target and its projections in signal spaces and the representations of the Fourier transform of the target in polar and Cartesian coordinates.

Basis of the DFI method is a mathematical analysis that shows the two dimensional Fourier Transform of the target and the one dimensional Fourier Transforms of the projected images of the target are identical. This result, known as the Projection-Slice theorem, applies to exact *continuous* representations of the target and is projections. In practical applications tomography works with noisy *discrete* measurements of projections. Recently techniques have been developed to implement inversion of discrete data with Fourier Transforms. FIG. 5 shows the key steps involved in the implementation of Direct Fourier Inversion (DFI). From the projection data it is straightforward to determine the Fourier coefficients of the target along a series of discrete points arranged on a polar raster: coefficients are given at equally spaced points along sets of rays from the coordinate origin in frequency space (see FIG. 5). However, to carry out a reconstruction efficiently, it is necessary to know the Fourier coefficients along sets of points distributed in frequency space on a Cartesian raster. Thus, efficient Fourier methods in tomography require a procedure for interpolation from a polar raster to a Cartesian raster. Inaccurate interpolation produces artifacts in the image, and can result in noise amplification. One of the key aspects of DFI implementation is the development of rapid highly accurate interpolation methods. Another important detail of the method is that the Fourier coefficients depend on the coordinate origin chosen for the spatial measurements. It is necessary to shift all transforms so that the origin corresponds to a common point. That origin is given by the point at which the rotation axis defining the view angles intercepts the target plane. Without the origin shift, the phases of the Fourier coefficients become scrambled in the inversion. Thus, the basic steps of the Direct Fourier Inversion Method are:

(1) 1D FFT: For protection data at a given angle, obtain the discrete, one dimensional Fast Fourier Transform with respect to the impact parameter. The result gives Fourier coefficients along a ray in signal space at equally spaced intervals from the origin up to some maximum frequency.

(2) Phase Shift to Target Origin: Bring the phase of the coefficients obtained in step (1) into agreement with a positioning convention that places the spatial coordinate origin at the axis about which the view angle was rotated.

(3) Fill Polar Raster: Repeat steps (1) and (2) for the projection data at each new view angle to build up the Fourier coefficients along a series of rays as shown in FIG. 5.

(4) Interpolate to Cartesian Grid: By interpolation determine values for the Fourier coefficients at equally spaced points in the two dimensional Cartesian grid.

(5) Phase Shift to Cartesian Origin: Perform a phase shift from the origin at the target center to an origin at the lower left corner of the square region in which the image will be constructed, as required by the convention for locating the origin in two dimensional FFTs.

(6) Inverse Fast Fourier Transform: Use the inverse FFT to convert from the frequency domain of the Fourier Transform back to signal space producing an image of the target.

In the basic form described above in steps 1-6 the DFI method can produce acceptable images only for targets in which the attenuation coefficient varies smoothly. However, numerous studies have in the past found that the direct Fourier inversion method, as described in steps 1-6, produces unacceptable images for practical targets, such as are found in medical applications, where sharp density variations are encountered between bone and soft tissue. Problems previously encountered arise from inaccuracy in the interpolation procedure, and from the basic problem that Fourier analyses tend to produce oscillatory artifacts when they encounter sharp discontinuities. Taken together these problems introduce unacceptable distortion and artifacts into the reconstructed images.

Related problems also affect reconstructions obtained using back projection methods. In fact the low-pass filters must be applied to correct artifacts that would otherwise contaminate the image generated by back projection methods without filtering.

Roberge and Flannery discovered a means to improve the DFI method to such a degree that it produces acceptable images that are comparable in quality with results obtained by FBP, while still maintaining the enormous speed advantage of DFI. Those steps are labeled by the terms "padding" and "filtering" in FIG. 5.

PADDING: prior to step (1) above we "pad" the projection data by adding additional data at impact parameters both smaller and larger than were actually observed. Since the target does not extend beyond the observed range of impact parameters, the values for the padded data do not need to be estimated; they are known exactly to be zero. Thus, by padding we are not introducing an approximation, we are using additional known information. We also use padding to assure that the number of data points in the projection are an integral power of 2, as required for optimum use of the FFT.

By padding we obtain values for Fourier co-efficients at more points along the ray in the polar raster. The number of points between the origin and the last frequency point increases by the padding factor. For instance, if we observed projection data at 256 impact parameters and padded the data by adding zeros at 256 more points, than we obtain 257 values for Fourier coefficients between the origin and the most distant point, rather than 129 without padding. Furthermore, the values at the intermediate points are approximately those values that would have been obtained using high order interpolation based on analyses of the behavior of Fourier coefficients at frequencies intermediate between discrete values. To apply those interpolation formulae at arbitrary intermediate points is possible, but computationally expensive. By padding we achieve the same accurate interpolation along rays and get points at many intermediate frequencies using the FFT algorithm itself. It is possible to adjust the amount of padding to meet the needs of the particular target being analyzed. By this step the interpolation procedure becomes far more accurate.

FILTERING: In order to remove or minimize the artifacts corresponding to oscillations introduced by using Fourier methods, a number of standard low pass digital filters have been developed. We find that the use of a standard low pass filter, e.g., the Hanning filter with adjustable cutoff frequency, effectively removes high frequency oscillations in the image. The Hanning filter smoothly reduces the amplitude of the Fourier coefficients by a factor Y(s) that varies smoothly from 1 to 0 as frequency grows from 0 to $s_c$:

$$Y(s) \begin{cases} 1/2(1 + \cos(\pi s/s_c)) & \text{if } s < s_c \\ 0 & \text{if } s > s_c \end{cases}$$

By choice of $s_c$ one can selectively adjust the cutoff of high frequency variations. (Note that the choice of low-pass filter in FBP methods serves the identical purpose). Filtering can be applied to the Fourier coefficients in either the polar or Cartesian grid, or both. Filtering essentially corresponds to averaging the reconstruction over length scales inversely proportional to the cutoff frequency. Viewed in this way it can readily be shown that filtering sacrifices resolution in order to improve the relative accuracy of values for the attenuation coefficient in the reconstruction. The choice of cutoff frequency $s_c$ can be chosen to adjust the degree of smoothing selectively.

It should be noted that the choices of filters can result in additional computational savings. It is unnecessary to evaluate Fourier coefficients beyond the cutoff frequency, or to carry out the inverse Fourier Transform for an unnecessarily large set of coefficients. For example, suppose that data was obtained sufficient to reconstruct the image on a grid of 512×512 pixels, corresponding to a maximum frequency s(512), but that is determined that the filter step needs to eliminate ½ the frequencies. Then the Fourier coefficients in the Cartesian grid need only fill an array of 256×256 points and the inverse transform can be carried out more rapidly using the smaller set 256×256 Fourier coefficients. Because of the advantages of DFI, we will use it to illustrate our invention.

SIGNAL TO NOISE AND IMAGE QUALITY CONSIDERATIONS

Signal to noise considerations place strict limits on several aspects of detector performance as well as ways in which they can be used for data acquisition.

Noise in tomographic images arises from two sources: (1) noise in the data, and (2) noise amplification introduced by the inversion method. The basic data consist of measurements of the attenuation of a signal, typically an X-ray beam, passed through the target along many coplanar rays, (L. A. Shepp and B. F. Logan, "The Fourier Reconstruction of a Head Section", IEEE Trans. Nucl. Sci., Vol. NS-21, pp. 21-43, 1974). FIG. 2 defines Cartesian coordinates in the frame of the target and a scanning device oriented to view the target from an angle $\phi$. Here $(t_1, t_2)$ define positions perpendicular to and along the path of the beam. For accurate inversion the attenuation measurements must have adequate signal-to-noise, and geometrical coverage of the scanbeams must fill the $(\phi, t)$ plane densely enough to give the desired resolution.

In the mode of operation preferred for high spatial resolution (plane parallel) data is obtained at M discrete, equally spaced view angles spanning $0 \leq \phi < \pi$, and N equally spaced, discrete, parallel impact parameters spinning $-D/2 < t_1 < D/2$, where D is the projected diameter of the target. The image recovered is divided into the pixels corresponding to a size, $\Delta t$, which in a preferred embodiment corresponds to a size given by $\Delta t = D/N$. It should be noted that the pixels exist on the display device, and the correspondence between their size on the object, $\Delta t$, and on the display device is a magnification factor m. Resolution in the reconstruction cannot exceed the pixel size $\Delta t$, and the rotation between views $\Delta\phi$ should be such that $D\Delta\phi/2 \leq \Delta t$, i.e. $M \geq N/2$. Data in this format can be used to reconstruct an image of the observed plane covering an area $\Delta D^2$ on a grid of order N×N pixels each of size $\Delta t^2$. Thus, $2N^2$ observations are used to map the target at $N^2$ points. For targets with unknown structure this degree of coverage in $(\phi, t_1)$ must be available to reconstruct the image with resolution $\Delta t$. However, targets with known symmetry require views, e.g., projections from a single view suffice to reconstruct images of rotationally symmetric targets.

For a discussion of signal-to-noise it is useful to define $\Delta x$ to be a spacing characteristic of the meaningful resolution allowed by the reconstruction. For FBP methods $\Delta x$ is given by the bandwidth used in the convolution step (D. A. Chesler, S. J. Riederer, and N. J. Pelc, "Noise due to Photon Counting Statistics in Computed X-Ray Tomography", J. Comput. Asst. Tomagr., VI, 64-74, 1977. For DFI methods $\Delta x$ is approximately the inverse of the cutoff frequency used in filtering.

While the propogation of noise from data to reconstruction can depend on peculiar features of the target itself that might introduce correlations into the reconstruction, general trends can be analysed objectively in terms of the algorithmic operations involved in the reconstruction. We define $\omega$ to be the ratio between noise-to-signal in the data and reconstruction, $$[\sigma_f/f]/[\sigma_P/P] = \omega(D, x, t) \quad \text{(Eq. 4)}$$

where we assume that the measured projection data are all typical magnitude P containing noise that can be described as normally distributed with standard deviation $\sigma_P$, and where $f, \sigma_f$ are the typical value of the reconstructed linear attenuation coefficient and its standard deviation.

Analyses to determine $\omega$ have been carried out by D. A. Chesler, S. J. Riederer, and N. J. Pelc ["Noise Due to Photon Counting Statistics in Computed X-ray Tomography", J. Comput. Asst. Tomogr. 1, 64 (1977)], for the FBP method, and by Roberge and Flannery for the DFI method. For both algorithims the amplification factor can be expressed as $$\omega^2 = B\left[\frac{D\Delta t}{\Delta x^2}\right] \quad \text{(Eq. 5)}$$

where B is a numerical coefficient of order unity that depends on details of the algorithm. Since inversion usually is applied near the resolution limit $\Delta x = \Delta t$ allowed by the scan data, Eq. 5, shows that noise amplification scales approximately as the square root of the number of pixels per side in the reconstruction, $K=D/\Delta x$, so that $\omega$ scales as $\sqrt{K}$ or $\Delta x^{-\frac{1}{2}}$. To image a target with higher resolution while maintaining fixed signal-to-noise requires more observations and higher accuracy. For example, to double the resolution at a fixed accuracy not only must measurements be made along four times as many paths, but also the signal-to-noise of each observation must be higher by $\sqrt{2}$. Eq. 5 also shows that methods that "average" the reconstuction ($\Delta x > \Delta t$), reduce noise. For instance, reconstructions that average 4 points, $\Delta x = 2\Delta t$, have $\frac{1}{2}$ the noise.

At the start of this section we noted that noise in tomographic images arises from two sources. The previous discussion quantified noise amplification introduced by the inversion method. Now we consider observational uncertainty in the data. Observational uncertainties in the data come from X-ray counting statistics as well as noise introduced by the detector. The two related measures of the accuracy, $\rho$, and the detective quantum efficiency, , may be used to quantify the amount of noise a detector adds to the X-ray signal. They are defined as $$\frac{\sigma_o}{S_o} \quad \text{(Eq. 6)}$$

$$\text{and } \mathcal{P}\left(\frac{S_o}{\sigma_o}\right)^2 / \left(\frac{S_i}{\sigma_i}\right)^2 \quad \text{(Eq. 7)}$$

where S means integrated signal, $\sigma$ = RMS integrated noise, and subscripts o and i refer to output signal of the detector and input X-ray signal, respectively.

In what follows we shall assume S and $\rho$ are in units of number of X-ray photons and that the photon source obeys Poisson emission statistics, i.e., photons are emitted at a constant average rate but at random times. Then the two measures are uniquely related by $$\rho = \frac{1}{\sqrt{\frac{S_i \mathcal{P}}{\sigma_i}}} \quad \text{(Eq. 8)}$$

We call $S_i$, the input number of X-rays needed to make the measurement, the *dose*. In general, both $\rho$ and $\mathcal{P}$ are functions of the dose, $S_i$, and a set of variables $(r_j, j=1, \ldots, n)$, which depend on the detector. Typically $r_j$ might be the area over which the signal is integrated, the integration time, the dose rate, etc. Given a plot of $\rho(S_i, r_j)$ one may derive a plot of $\mathcal{P}(S_i, R_j)$ and vice versa. Consequently, a choice between the two measures is based largely on convenience.

The detective quantum efficiency has been used for years by the electro-optics industry as a characterization of imaging devices. Its use as a measure of two dimensional X-ray detector efficiency has been discussed by Gruner and Milch [Transactions Amer. Crystallographic Assoc. V18, P149 (1982)]. It describes the added noise introduced by the detector relative to an ideal detector. The output statistics of the ideal detector are defined equal to the input signal statistics, i.e., $$S_o/\sigma_o = S_i/\sigma_i \quad \text{(Eq. 9)}$$

in which case $\mathcal{P}=1$. The degree to which $\mathcal{P}$ is less than 1 indicates the fractional manner in which the detector is less than ideal. For the electro-optic X-ray detector used in the microtomography system it is preferred that $\mathcal{P}$ be greater than 0.05. It is more preferred that $\mathcal{P}$ be greater than 0.5.

If the detector is exposed for a time T, then the total number of photons incident to the detector is $N_D = I_D T$, and the standard deviation $\sigma_N$ expected for N photon is $\sigma_N = N^{\frac{1}{2}}$. If on average, the number of counts observed in a time T ought to be $\overline{N}$ then the measured number will be $N = \overline{N} + \tau[\mathcal{P}\overline{N}]^{\frac{1}{2}}$ where $\tau$ is a normally distributed random variable. Then measured projection will contain Gaussian noise according to $$P = \overline{P} + \tau[\overline{N_D}\mathcal{P}]^{-\frac{1}{2}} \quad \text{(Eq. 10)}$$

where $\overline{P}$ is the average expected value.

For a target of typical diameter D and average linear attenuation coefficient $\overline{F}$, the results assembled so far determine $N_O$, the number of incident photons per pixel needed to produce a reconstructed image with signal-to-noise ratio $f/\sigma_f$. Equations 1 and 2 show that $P = \overline{F}D$, and that $N_D = N_o \exp(-\overline{F}D)$. Then from Eq. 4 we find that $$\frac{N_0}{\omega^2} = \frac{\exp(\overline{F}D)}{\mathcal{P}[\overline{F}D\,(\sigma_f/f)]^2} \quad \text{(Eq. 11)}$$

Recall that the amplification factor $\omega$ (see Eq. 5) depends essentially on the image size in pixels. Thus, for a reconstructed image of given pixel size and accuracy, $\sigma_F/F$, $N_0$ depends only on the optical depth $\overline{F}D$ through the target.

Figure 6:
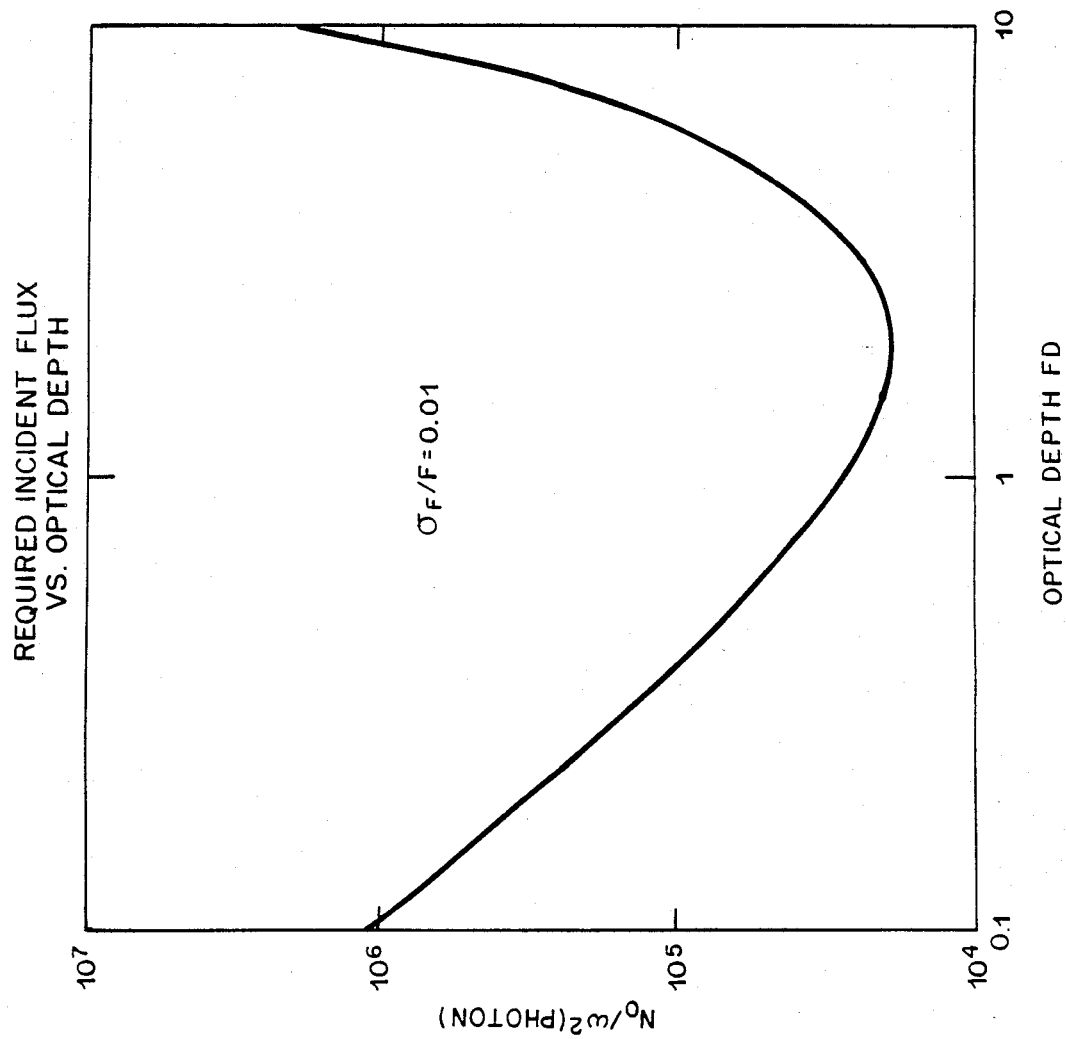
FIG. 6—Incident photons, $N_O$, required per projection measurement plotted as a function of optical depth through the target, FD. For Possion counting statistics, $N_O$ incident photons are needed to provide sufficient accuracy for reconstruction of a tomographic image with relative accuracy $\sigma_F/F = 0.01$. The factor is the ratio between relative accuracy in the image and projection data. For a Direct Fourier Inversion of an image with 100×100 pixels, $\omega^2$ is greater than 10.

As shown in FIG. 5, $N_0$ is a minimum for optical depth $\overline{F}D = 2$. The plot shown in FIG. 6 is for a signal to noise ratio $\sigma_f/f = 0.01$, however similar behavior is found for all useful signal to noise ratios. This occurs because the actual signal depends on the number of photons absorbed by the target. For large optical depth, $\overline{F}D \gg 2$, $N_0$ grows because few photons are transmitted. For small optical depth, $\overline{F}D \ll 2$, $N_0$ grows because few photons are absorbed.

Further substitution for $\omega$ from Eq. 5 into Eq. 11 gives an expression for $N_0$ when the image is reconstructed on a grid of $D/\Delta x$ pixels per side:

$$N_0 = B\left[\frac{D}{\Delta x}\right]\left[\frac{t}{\Delta x}\right]\frac{\exp(\overline{F}D)}{\mathcal{P}[\overline{F}D(\sigma_f/f)]^2} \quad \text{(Eq. 12)}$$

For example, to image a target of optical depth $\overline{F}D = 1$, with relative accuracy $\sigma_F/F = 0.01$, on a grid of size $100 \times 100$ pixels requires $N_0 \approx 10^6$ incident photons per pixel in the detector (when $\Delta x = \Delta t$).

X-RAY SOURCE REQUIREMENTS

The previous discussion shows that $N_0$, the number of photons incident per pixel required to produce an acceptable tomographic image depends sensitively on the optical depth ($\overline{F}D$) which varies strongly with sample size, composition, and beam energy. Optimal observation conditions occur when $\overline{F}D=2$. The preferred range of optical depths lies between $\overline{F}D=0.2$ and $\overline{F}D=6$. A more preferred range of optical depths for sample observation lies between $\overline{F}D=0.8$ and $\overline{F}D=3$. This range of observational conditions can be attained either by altering the X-ray beam energy or the sample size. The sample size is $D=N\Delta t$ where $N=N_{image}$ is the number of pixels across the object and $\Delta t$ is spatial resolution of each pixel. For the tomography systems described herein, $N_{image}$ is in the range of 20 to 5,000. A more useful range of $N_{image}$ lies between 100 and 1000. The maximum attainable resolution for the tomography system described herein is 0.5 microns and the minimum attainable resolution is approximately 5 mm. A more preferred mode of operation of the instrument provides resolution ($\Delta t$) in the range of 1–100 microns. The minimum sample size which can be accommodated by the instrument is 10 pixels $\times$ 0.5 microns = 5 microns and a more preferable minimum sample size is 100 pixels $\times$ 1 micron = 100 microns. To operate the instrument near optimal observation conditions ($\overline{F}D=2$) with samples having dimensions greater than or equal to the minimum sample size, the linear X-ray absorption coefficient, ($\overline{F}$), through the sample, should be less than 4,000 or more preferably less than 200. To obtain linear X-ray absorption coefficients ($\overline{F}$), below these limits, the X-ray energy should in general be greater than 1 kev and more preferably greater than 5 kev. These limits are derived from the mass attenuation coefficients of X-ray in matter which can be found several standard references including the *Handbook of X-rays*, edited by E. F. Kaelble (published by McGraw Hill Book Co., New York, 1967).

Sources of X-rays with energies greater than 1 to 5 kev include synchrotrons, rotating anodes, X-ray generators and X-ray tubes. To use these sources of radiation in a preferred embodiment for which the device acts as a microtomography system, the X-ray beam generated must be conditioned so that it is plane parallel with a predetermined spectral distribution. Parallelism of the rays is required due to the nature of the reconstruction algorithms which require that rays pass through only a single column of pixels in the sample. As such, a principal ray passing through the sample (see FIG. 3) must be parallel with any other ray through another point in the sample with an accuracy given by $$\alpha < \frac{\Delta t}{D} \times 2 \qquad \text{(Eq. 13)}$$

where $\alpha$ is the maximum angular deviation of two principal rays through different points in the sample, $\Delta t$ is the minimum resolution element in the image and D is the distance the X-ray beam travels through the sample. Divergence of any two rays passing through the same point in the sample is limited by penumbral blurring of the shadow cast onto the detector. To maintain desired resolution, the divergence of the two rays through the same point in the sample must be such that $$\alpha' < \frac{\Delta t}{S} \qquad \text{(Eq. 14)}$$

where $\alpha'$ is the angular divergence of two rays through the same point in the sample and S is the distance from the sample to the first energy conversion element in the detector.

Different collimation techniques can be used to achieve this degree of parallelism and beam divergence for rotating anodes and X-ray tubes. Collimation can be achieved by using either a monochrometer, physical collimator or distance to limit the angular beam spread through the sample. Collimation increases as the distance between sample and source is increased. If the effective source size at the X-ray generator is $s_{generator}$, the distance a sample must be placed away from the generator, $d_{generator}$, (determined from Equation 14) is $$d_{generator} > \frac{(s_{generator})}{t} S \qquad \text{(Eq. 15)}$$

Collimation can also be achieved by placing in the beam, either a grazing incidence X-ray mirror, layered synthetic multilayer monochrometer, flat crystal monochrometer or curved crystal monochrometer. Positioning of these X-ray optical elements should be such that both Eqs. 14 and 15 are satisfied and flux through the sample maximized to the greatest extent possible. Choice of collimation method used for rotating anodes and X-ray tubes is dictated by not only by these requirements but also by the degree of spectral purity required for accurate image reconstruction. Spectral purity in beams collimated with distance can be achieved by filtering of the radiation. For instance, a nickel filter can be used with a Cu X-ray tube to improve the spectral purity. For synchrotron radiation, the angular distribution of radiation emanating from the ring is sufficiently small that in many cases no additional collimation is required. However, because of the high brightness of synchrotron sources, it is usually desirable to utilize a monochrometer to improve the spectral purity of the radiation.

ACQUIRING PROJECTION MEASUREMENTS WITH AN ELECTRO-OPTIC X-RAY DETECTOR

To acquire projection measurements needed for tomographic reconstructions, several detector attributes must be known and often compensated for. Detector attributes which can significantly affect acquisition of accurate projection measurements are: (1) positional linearity (geometric linearity), (2) detector alignment (spatial orientation), (3) spatial resolution, (4) useful dynamic range of the detector, (5) signal dependent backgrounds in the recorded image, (6) spatial uniformity of detector response, (7) linearity of response vs. intensity, (8) sample alignment. Most of these detector attributes are of importance only for imaging detector systems and can be ignored in non-imaging detectors such as those used in medical CT.

(1) Postional Linearity (geometric linearity)

Imaging electro-optic detectors contain pixels arrayed in linear or planar fashion. Geometric distortions from true positional linearity of the pixels within the detector can introduce artifacts in reconstructed images. Artifacts are introduced from uncorrected positional non-linearities because the impact parameters, $t_1$, (see FIG. 2) are systemmatically mismeasured. This mismeasurement occurs whenever a Cartesian grid imaged through an electro-optic detector deviates from linearity by more than 1 pixel position. For small deviations from true positional linearity a distortion map can be applied to correct the impact parameters so that data is acquired in a true Cartesian grid. The distortion map is applied as a mathematical interpolation between the measured points. The amount of interpolation required between points is determined from measurements of the distortion of a true Cartesian grid imaged through the electro-optic detector. This correction becomes impractical when the deviation from linearity exceeds 10 pixel positions across the detector surface. As such, it is preferred that deviations from true linearity be less than 10 pixels in the recorded image and this deviation be corrected with a distortion map. In a more preferred embodiment impact parameters are accurately measured at the detector surface and the maximum deviation from geometric linearity is less than 1 pixel in the recorded image with no distortion map being required to correct the data.

(2) Detector Alignment (spatial orientation)

The imaging electro-optic detector should be aligned so that the axis of the Cartesian grid of pixels in the detector are parallel and perpendicular to the axis of rotation within the tomography system. Depending upon protocols for data acquisition, the axis of rotation within the tomography system can be either the sample axis of rotation or the axis of rotation of the source and detector. When the system axis of rotation and detector are misoriented by small amounts, resolution is degraded. Angular misorientations between the system axis of rotation and a two dimensional imaging detector can be measured by comparing two images of a regular object separated by a 180° rotation. Differences in the line of centroids of the object taken in these two views determine the axis of rotation projected onto the detector. In principle the axis of rotation should lie along either a row or column of pixels within the detector. Corrections for angular misalignment between detector and system axis of rotation should be made when the angular misalignment exceeds $8\Delta X/d$ radians where $\Delta X$ is the system resolution in pixels and d is the number of pixels across the maximum diameter of the object about the rotation axis. Corrections of angular misalignment are made by mathematically transforming the data array read from the detector with an angular rotation algorithm which aligns the axis of rotation or by physical rotation of the detector with respect to the axis of rotation. In the preferred embodiment, the detector is angularly aligned with the system axis of rotation so that the data does not have to be mathematically corrected. In a more preferred embodiment (where the angular misalignment is matched to the resolution of the device), the angular misalignment is less than $2t/d$, where t and d are referenced to a cartesian coordinate system. This correction can be done with an angular tilt stage which either moves the detector or rotation stage. In any event, the angular misalignment between the Cartesian grid of points on the detector and the system axis of rotation must be accurately measured.

In some cases the rotation axis is not fixed in space as the sample turns. When the rotation axis drifts in space, the apparent position of the rotation axis on the electro-optic detector will drift when measured for several angular rotations. This drift is usually due to imperfections in the rotation stage, which lead to wobble and tilt during angular rotation. Preferably a rotation stage is choosen which does not exhibit spatial drifts in the rotation axis; however this is not always possible. To eliminate mechanical drifts, a mathematical transformation can be applied to the measurements. By measuring the rotation axis drift and angular misorientation it is possible to either mechanically or mathematically reduce the apparent maximum displacement of any point along the observed rotation axis to less than $4\Delta X$, where $\Delta X$ is the resolution of the detector measured in pixels.

In a more preferred embodiment, the maximum uncorrected drift of any point along the rotation axis is less than $\Delta X$. When there is a mechanical drift in the axis of rotation projected onto the detector, the angular misalignment is taken to be the average angular misalignment over a 180° rotation.

It should also be noted that the rotation axis should be aligned along one of the pixel rows of columns near the center of the detector. Aligning the rotation axis near the detector edge severely restricts usable sample size. To move the rotation axis on the detector, either the detector or rotation stage can be physically translated.

(3) Spatial Resolution

Figure 7:
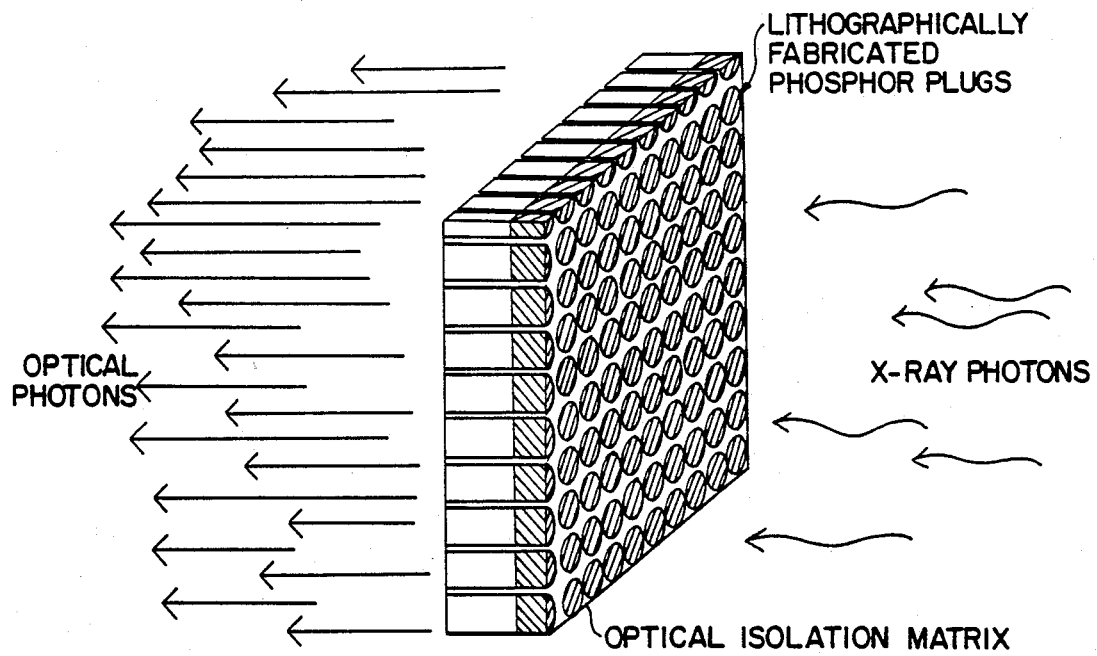
FIG. 7—Schematic diagram of cellular phosphor screen used to obtain high spatial resolution images.

Spatial resolution of the detector is determined primarily by the format alteration technique used to couple the energy convertor plate and readout device of the electro-optic detector. Adjustability of the detector resolution through simple format alteration is a key advantage of electro-optic x-ray detectors over the more conventional scintillation detectors which have been used in medical tomography. Format alterations can be performed using either electron or light optics. Simplest of all format alteration techniques is a lens system which couples light from a phosphor screen directly onto a readout device with no intervening image intensifier. This system is well-suited for magnification of images formed at high resolution phosphor screens and can achieve spatial resolutions comparable to the wavelength of light (approximately 0.5 microns). This limiting spatial resolution can only be achieved with extremely high resolution phosphor screens which are ideally formed as a honeycombed array of phosphor plugs having dimensions smaller than the desired spatial resolution. FIG. 7 shows a schematic diagram of a high resolution cellular phosphor screen. High resolution is achieved with cellular phosphor screens because light emission is localized within the dimensions of a single phosphor cell. In flat phosphors light is not spatially localized and can propagate within the plane of the phosphor degrading spatial resolution. By fabricating the phosphor screen as a honeycombed array of individual phosphor cells degradation of resolution by light scattering within the phosphor can be eliminated. For cellular phosphors the limiting resolution is often determined by the numerical aperture of the relaying lens system which can be 0.6–0.8, yielding ultimate spatial resolution of approximately 0.5 microns. Lower resolutions can be achieved by decreasing the magnification of the lens system and coarsest resolutions are achieved by using demagnifying rather than magnifying lens systems. These same principles apply to systems which use electron optics rather than light optic to alter the image format. In general, it is preferred that the format alteration have a spatial resolution that is less than 5 pixels on the detector. In a more preferred embodiment, the format alteration section is chosen to have a spatial resolution of less than 1 pixel on the detector.

Focusing of the image format alteration device can also affect detector spatial resolution. Optimum resolution is obtained when images from the format alteration device are sharply focused on the electro-optic readout device. To evaluate focusing within the detector, projection measurements can be analyzed for high contrast targets with spatial frequencies comparable to the expected spatial resolution. Simple useful high contrast targets are woven mesh metallic screens, which may be sequentially stacked with angular misorientations to increase spatial frequency of the pattern. By maximizing X-ray image contrast between transparent openings in the mesh and the opaque wires, the image from the format alteration device can be sharply focused. When the image is not sharply focused in the detector, useful resolution of the tomographic scanner can be severely degraded. Thus, the image format alteration device must be carefully focused with respect to the electro-optic readout device prior to recording images of transmitted radiation which are used to obtain projection measurements.

A more quantitative evaluation of the spatial resolution obtained from a focused electro-optic detector can be obtained by measuring the modulation-transfer function of the complete tomographic scanner. The modulation transfer function is the ratio of recorded contrast to original contrast for different frequency sine waves modulations of the incident x-ray intensity where $$\text{Contrast} = \frac{I_{max} - I_{min}}{I_{max} + I_{min}}$$

and $I_{max}$ ($I_{min}$) is the maximum (minimum) intensity in the sine wave pattern. The frequency dependence of this contrast function provides a unique characterization of the image quality produced by the system. At high frequencies, the function will smoothly fall from a value near one to zero and the frequency at which the MTF is 0.5 can be taken as the spatial resolution $\Delta X$ of the system. The MTF can also be used to evaluate focusing within the detector. The detector is considered focused when the measured resolution is within a factor of 4 of the resolution obtained at best focus. In a more preferred embodiment, the measured resolution is within a factor of 1.5 of that obtained at best focus. In this application, the detector resolution, $\Delta X$, will be taken to be the resolution obtained at best focus. On a preferred embodiment the resolution at focus, $\Delta X$, is less than two pixels, ensuring a large number of real resolution elements across the image. At low frequencies (long wavelength), the small deviation between the MTF and 1 is a direct measure of the useful dynamic range of the system with $$\text{Useful dynamic range} = \frac{2}{1 - MTF}$$

Another and perhaps more useful definition of the useful dynamic range of the detector is the ratio of the maximum signal level recorded in an exposure to the sum of all signal dependent backgrounds and noise sources (other than counting statistics).

(4) Useful Dynamic Range

By minimizing noise from sources other than counting statistics, the useful dynamic range is maximized. Examples of noise sources other than counting statistics are readout and dark noise. Dark noise accumulates with time in the absence of an input signal and can severely limit maximum exposure times. Readout noise is an uncertainty added to the signal during readout of the sensor used to record optical images. Since it was shown that under optimal observation conditions signals with an optical density of 2 (13% transmission) must be recorded, the detector must be operated in a manner such that the useful dynamic range is greater than 10. In a more preferred embodiment, the detector is configured and operated in a manner such that the useful dynamic range is greater than 50. To obtain such useful dynamic ranges, the dark noise accumulated during exposure should be a factor of 10 less than the recorded signal. To satisfy this condition, the incident x-ray intensity must be chosen to be sufficiently large to insure that appreciable dark noise does not accumulate in the detector. In a more preferred embodiment, the dark noise accumulated during the exposure should be a factor of 50 less than the recorded signal.

(5) Signal Dependent Backgrounds

Signal dependent backgrounds can also limit the useful dynamic range of the detector. A signal dependent background exists in all electro-optic x-ray detectors due to scattering of radiation between the energy conversion process and detection at the electro-optic readout device. Scattered radiation produces a signal dependent background component which is spatially correlated with the signal as well as a component which is spatially uncorrelated with the original signal. Because optimal observation conditions occur when the optical density through the target ($\overline{FD}$) is nearly equal to 2 (13.5% transmission), the total signal dependent background (correlated+uncorrelated) in any pixel covered by the sample must be less than 10% of that from the unattenuated x-ray beam. In a more preferred embodiment, the total signal dependent background (correlated+uncorrelated) in any pixel covered by the sample is less than 2% of the signal derived from the unattenuated x-ray beam. Signal dependent backgrounds for an electro-optic x-ray detector can be measured using a variety of techniques. A simple technique is to cover half the incident x-ray beam with a mask which totally absorbs x-rays. In principle, there should be no signal in the region covered by the mask, and signal levels detected in the region behind the mask are clearly due to the correlated and uncorrelated backgrounds. Far from the mask edge the signal dependent background slowly varies and is primarily due to the uncorrelated signal level. Near the mask edge spatial variation of the signal dependent background is a direct measure of the correlated scattered light. Thus, by fitting a spatial correlation function to the signal dependent background near the mask edge, the correlated and uncorrelated signal dependent backgrounds can be quantified.

For lens coupled detectors, scattered radiation can be significantly reduced by coating all optical surfaces with an anti-reflection coating. This is especially important in the vicinity of the optical readout device. In this region, reflected light can readily reenter the readout device. For example, in a preferred embodiment where a CCD is used as the readout device, retroreflection of light backscattered by the chip can limit the useful dynamic range to 100-500:1. For front illuminated CCD's more than 40% of the incident light may be backscattered from the CCD surface into the optics, while back illuminated CCD's only backscatter half as much light. Front illuminated CCD's detect light incident through the gate structure on its front surface while back illuminated devices are thinned to 10 micron thickness and illuminated through the flat rear surface. If 1-2% of the light is retroflected from the optics than the useful dynamic range will be limited 100-200:1, for front illuminated CCD's and 200-500:1 for back illuminated CCD's.

It is seen that signal dependent backgrounds can be directly measured. They can be reduced by (1) designing the apparatus to minimize scattered light and (2)

scattered light effects can be stripped away from measured data using a mathematical filter function.

(6) Spatial Uniformity of Detector Response

Most detectors are not unformally sensitive across their area. If non-uniformity of response between adjacent pixels in not calibrated out of the data, then artifacts will be generated in the reconstruction process. A stable 10% non-uniformity between adjacent pixels is easily calibrated out of the data. However, when the non-uniformity of response between adjacent pixels exceeds 75%, calibration methods fail to work. Failure of calibration methods for deeply modulated non-uniformities between adjacent pixels is due to stability considerations of the detector. Vibrations, spatial drifts, and time dependent drifts of the sensitivity, all decrease the stability of the detector so that deeply modulated non-uniformities between adjacent pixels cannot be readily removed from the data. As such, it is preferred that the non-uniformity of response between adjacent pixels be less than 75%. Limits also exist on variations of the locally averaged sensitivity across the detector surface. The locally averaged sensitivity is defined as the average of the sensitivity of a pixel and its immediately adjacent neighbors. From signal to noise considerations it is preferred that the locally averaged sensitivity varies by no more than a factor of 2 across the entire detector surface. Variations in the locally averaged sensitivity across the detector surface lead to a variation in the detected signal to noise ratio. To optimize performance of the device it is desired that the fewest possible x-ray photons be required for reconstruction of a target at a given signal to noise ratio. When the locally averaged sensitivity varies across the detector, the required number of x-ray photons correspond most closely with that expected for the minimum average sensitivity. Regions of minimum locally averaged sensitivity generally correspond to defects in the detector. Thus, to minimize exposure time and optimize performance of the tomography system, it is desired that the variations in the locally averaged sensitivity across the detector be less than 10 and in a more preferred embodiment be less than 2.

A persistent error in response at a fixed position on the detector introduces a ring type artifact into reconstructed images. Ring artifacts are introduced into the reconstruction if the response of adjacent pixels differs in a manner that is not accurately correctable. Such an error can arise due to lack of spatial uniformity in the detector. FIG. 8 shows a mathematical simulation of ring artifacts in the reconstruction of a sandstone sample. Projection data for the sandstone were mathematically simulated. Successive reconstructions of the target were obtained with the addition of 1, 5, 10 and 50% modulations added to projection data in isolated pixels. At impact parameters where the excess modulation was added, a ring artifact appears in the reconstructed image. Inspection of FIG. 8 shows that if pixels have projection measurements mismeasured by more than 1% a ring artifact will be clearly visible in the image. To avoid this problem, it is preferred that spatial uniformity of detector response be correctable to better than 1% of its nominal value over the entire detector. Correction of detector uniformity of response can be made using a calibration frame which is acquired when the sample is withdrawn from the beam. To process this calibration frame, the correction sequence shown in FIG. 9 can be used when the detector responds linearly to the incident x-ray flux. This processing sequence first removes (FIG. 9—step 1) zero offset effects (dark count, etc.) by offsetting the signal so that the corrected signal vanished when the incident x-ray flux equals zero. This correction is made for every pixel in the image and is performed by subtracting a frame, $D(t)$, with the required offsets from both the calibration frame and transmitted intensity measurement. To acquire this zero offset map, $D(t)$, the detector can be exposed with no incident x-ray flux. Sometimes, when a CCD is used in the electro-optic detector, a very low signal level is required to establish the offset frame $D(t)$, because of well known "fat" zero effects. Following the zero offset correction, some of the effects of detector spatial uniformity are removed (FIG. 9—Step 2) by correcting the data with a flat field gain map. The gain map is designed to correct spatial response variations of all elements in the detector except for the energy conversion element. A gain map for the CCD based electro-optic detector shown in FIG. 10 can be obtained by removing the phosphor-plate and recording a spatially uniform optical beam. Such a beam can be generated from a point optical source which is far from the detector. The correction with a gain map would be redundant if scattered light effects did not have to be removed from the image. To remove scattered light effects (FIG. 9—Step 3) a spatial filter function, F, can be designed which mimicks the effect of light scattering within the detector. The filter function generates a correction from, F, whose values depend directly on the data in the unfiltered frame. A simple filter function is a spatial high pass filter which has a correlation length that is determined by the spatial extent of light scattering in the system. The amplitude of the filter function is determined by the intensity of light scattering which is typically less than 4%. Before projection measurements can be obtained from the data, the grey scale level should be normalized (FIG. 9—Step 4) to the average value in a region of the image not obscured by the sample. This normalization factor [$\beta_o$ and $\beta_r$ for the calibration frame and intensity measurements, respectively] removes time dependent variations in the x-ray source intensity. Finally, the projection measurements are determined from the ratio of the fully corrected calibration frame and intensity measurement.

Figure 9:
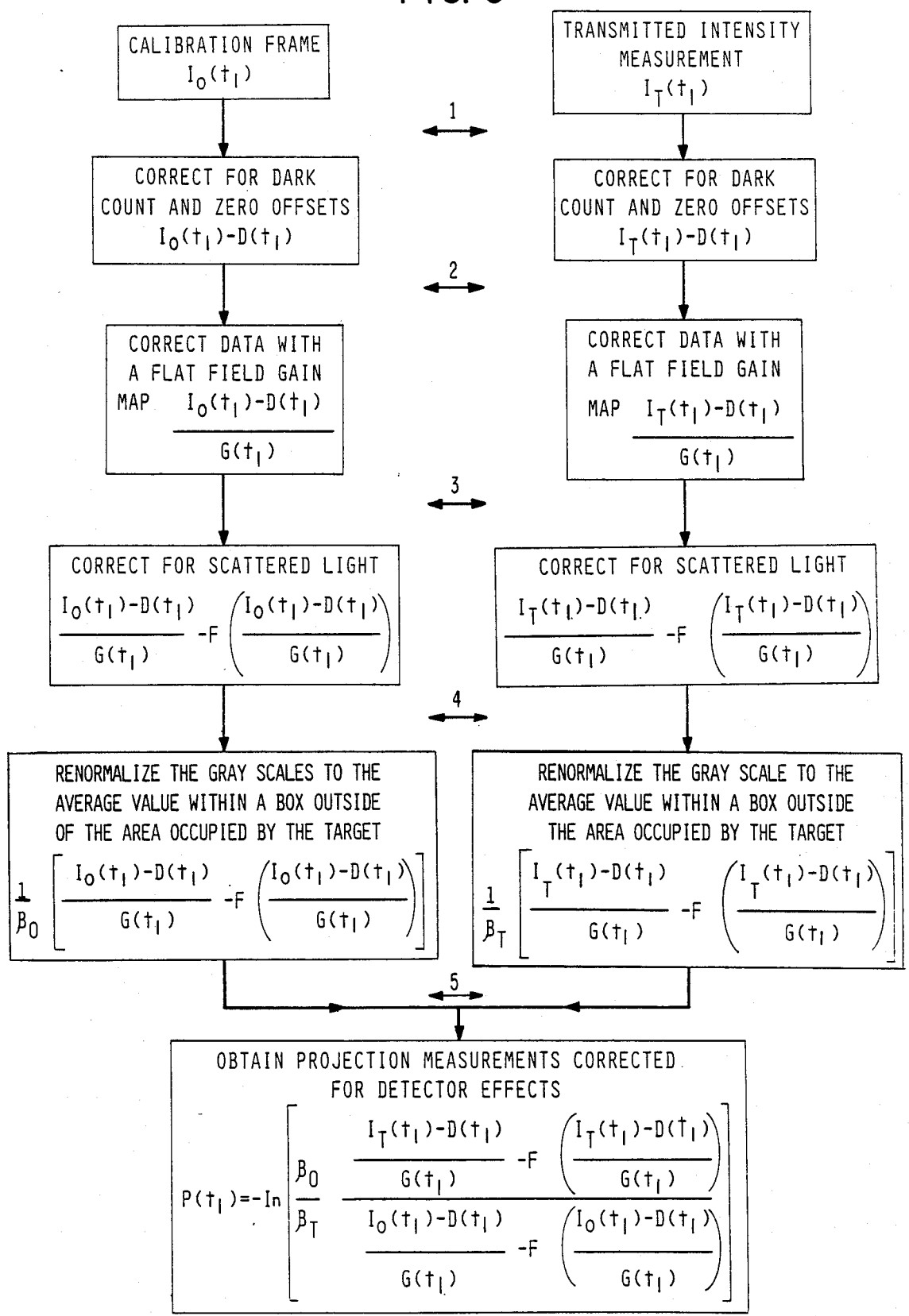
FIG. 9—Processing sequence for measurement and calibration to remove pixel to pixel response variations as well as a substantial portion of scattered light effects.

It should be noted that when scattered light accounts for only 1–3% of the signal derived from the unattenuated beam and the pixel to pixel variation in detective quantum efficiency is less than 3%, one can usually omit steps 2 and 3 of the sequence shown in FIG. 9. In this case, the scattered light correction becomes small and ring artifacts do not obscure information in reconstructed images.

Amplitude of ring artifacts can be limited to less than 10% of the local attenuation coefficient values in reconstructed images by following the described design criteria and calibration procedures. At values above 10%, ring artifacts severely obscure the local image and thus it is preferred to limit them to values below 10%.

When cellular phosphors are used in the detector, pixel to pixel gain variations introduced by the cellular structure can be reduced by rapidly moving the phosphor back and forth across the x-ray beam. This movement has the effect of averaging out variations in the cell structure projected on the detector. Several of these cycles need to be repeated within a single frame exposure time. By incorporating a translation device on a cellular phosphor, intensity of ring type artifacts can be reduced.

(6) Linearity of Response vs. Intensity

The detector response vs. X-ray intensity must be linearized to accurately measure the projections which are defined in Eq. 2. The projection measurements form the basis for the tomographic inversion methods. Projection measurements can only be accurately obtained when the detector response is linearized. Detector response vs. incident X-ray dose can be linearized by appropriate calibration methods when the deviations from linearity are less than 25% over the useful dynamic range of the detector. When deviations from linearity exceed 200% anywhere within the usefuly dynamic range of the detector, calibration techniques fail to adequately correct the data. Failure to adequately linearize the detector response when deviations from linearity exceed a factor of 2 generally stem from change of the response with time. It is preferred that the corrected detector linearity be better than 5% over the useful dynamic range. Correction for detector linearity must be applied directly to all measurements before using the type of processing sequence outlined in FIG. 9. In a more preferred embodiment, linearity of the detector after calibration correction is better than 0.5% over the useful dynamic range.

(7) Sample Alignment

The sample being studied must be aligned so that its centroid is on or near the rotation axis. This alignment can be accomplished by mounting a goniometer between the sample and rotation stage. The sample is then viewed during rotation and centered on the rotation axis by mechanical translation. The sample must be well centered and small enough that it does not move outside the detector field of view during a complete 180° rotation.

EXAMPLES

Example 1

Figure 10:
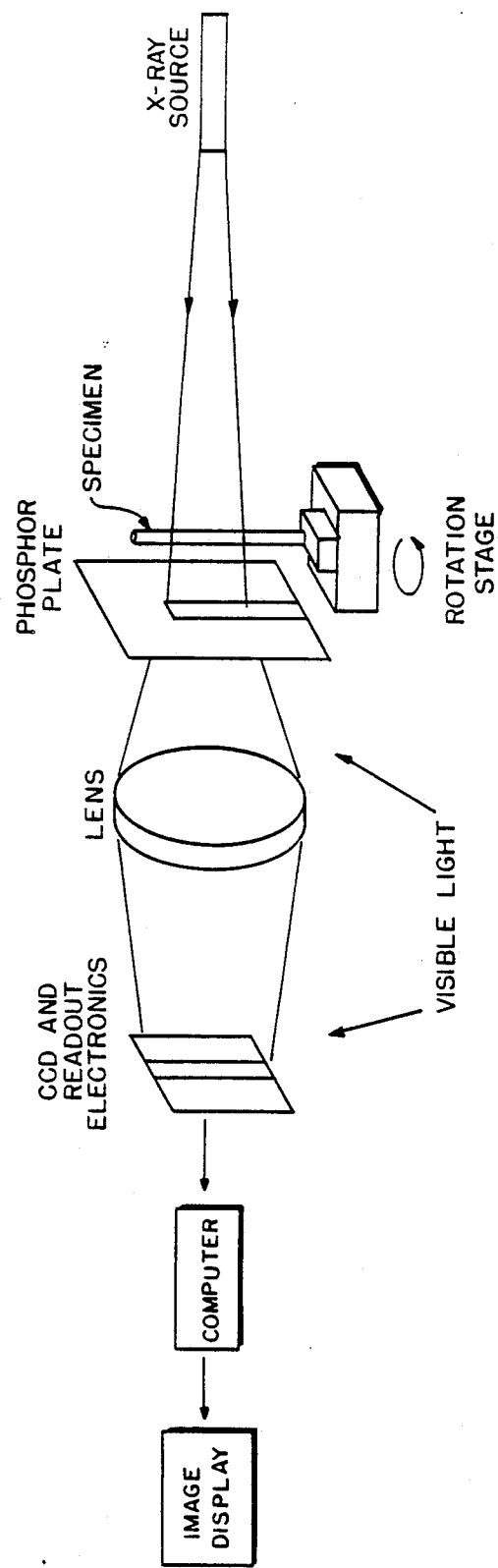
FIG. 10—Schematic diagram of an X-ray microtomography apparatus constructed with an electro-optic detector.

The X-ray microtomography system shown in FIG. 10 was used to examine a 750 micron hollow glass tube packed with 200 micron silica spheres along with a 10 micron tungsten wire which ran along the axis of the tube. The electro-optic detector shown in FIG. 10 consists of a phospor conversion plate, lens system and CCD based readout device. X-rays were generated from a Cu fine focus X-ray tube manufactured by Phillips Electronic Instruments. The tube was aligned to present a point X-ray source to the experiment and was operated at a power of 1.5 kw. The distance between X-ray source and specimen was chosen to be 20 cm and the tube was positioned so that the line connecting the center of the point X-ray source was within 1 mm of the optical axis of the lens system. Take-off angle of the experiment with respect to the anode shadow projected by the tube was approximately 5° yielding an effective X-ray source size of approximately 750 microns by 500 microns. The sample was held on a rotatable goniometer within the X-ray beam. The rotation stage was controlled with stepping motors which can move the stage in increments as small as 0.01°. For a full 360° rotation of the rotary stage, wobble in the axis of rotation was less than $10^{-5}$ radians. For such an infintesmal wobble, the axis of rotation remains fixed in space and does not translate as the sample is rotated. On the goniometer the sample was aligned so that it remained within the lateral field of view as the sample was rotated. A phosphor conversion plate was located 2 mm behind the sample. The phosphor was a 5 micron thick layer of evaporated CsI doped with thallium. Light emanating from the phosphor conversion plate was imaged by a photographic lens onto a charged coupled device. The CCD used in these experiments was a RCA SID-501 which has 336 by 540 active pixel elements.

In using this system, the following detector attributes must be considered:

(1) Geometric Linearity

No correction for geometric linearity had to be applied to data taken with this detector because the lens system was distortion free and pixels in the CCD were accurately arranged on a cartesian grid.

(2) Detector Alignment

The CCD was aligned so that its columns were parallel to the sample axis of rotation. This alignment was determined by comparing two images of the sample taken before and after rotation through 180°. By measuring centroids of the sample in these two frames, the axis of rotation was located at several rows to ±½ pixel. The axis of rotation originally did not lay along a column of the detector, so the CCD was rotated within its cryostat. After rotation, the axis of rotation was within ±½ pixel of column 201 of the detector.

(3) Spatial Resolution

To maximize detective quantum efficiency a photographic lens with a f number of 1.4 was chosen. Magnification of the lens system was adjusted so that an 8 micron element on the phosphor plate was magnified to 30 microns which is the pixel size of the CCD. The lens element was focused on the phosphor plate by maximizing contrast in the X-ray image of a wire mesh screen (25 um openings). Spatial resolution of this system corresponds accurately to one pixel in the detector. Diffraction limited resolution of the lens systems was 2.8 $\mu$m, while light spreading in the flat phosphor limited resolution to 5.8 $\mu$m. It should be noted that resolution is not degraded by width of the penumbral shadow cast by the sample onto the phosphor. At most, the penumbral shadow extends over 5 $\mu$m, for the geometric arrangement of source, sample and detector. With this geometric arrangement of the apparatus, the angular deviation, $\alpha$, of 2 principle rays through different points in the sample was $2.5$ times $10^{-2}$ radians, which as required by Equation 13 is significantly less than $2\Delta t/S = 4.26 \times 10^{-2}$ radians. Angular divergence, $\alpha'$, of 2 rays through the same point in the sample is $3.75 \times 10^{-3}$ radians which as required by Equation 14 is less than $\Delta t/S = 4 \times 10^{-3}$ radians. Thus, data is acquired in multiple stacked planes in the plane parallel mode. The number of equally spaced view angles, M, required for data acquisitioned in this mode, must be greater than N/2, wherein N is the number of equally spaced discrete parallel impact parameters spanning the target. Since the target is 750 microns in diameter and each pixel spans 8 microns, approximately 85 impact parameters span the target. To satisfy the protocol for data acquisitioned in the plane parallel mode, 240 equally spaced view angles, $\Delta\phi$, were chosen to scan the target.

(4) Detective Quantum Efficiency

Detective quantum efficiency of the detector was measured to be 0.75 and the total signal dependent background was found to be less than 2 percent of the signal from the unattenuated x-ray beam. Useful dynamic range of this detector configuration was a factor of 80 and the maximum non-uniformity of response between adjacent active pixels was less than 1 percent.

These parameters were obtained because all of the optical elements were coated with an anti-reflection layer and stray light in the system was absorbed with optical baffles. Also, the CCD was back illuminated, significantly reducing the amount of back-scattered light. Useful dynamic range was only limited by the small amount of scattered light, reflected from the CCD surface. Data, with a noise to signal ratio of 0.3% was obtained in the detector by exposing each view angle for 3 minutes. Data from each view angle was digitized with a 16 bit analog to digital convertor, processed by a computer and stored on magnetic tape.

(5) Signal Dependent Backgrounds

A signal dependent background was measured by inserting a lead foil which covered half the active area of the detector. Far from the lead foil edge there existed a spatially uncorrelated signal dependent background of 7.5% of the incident x-ray flux. The signal rose as the foil edge was approached and the rate of rise could be fitted with a high pass filter function that had a correlation length of 8 pixels and an amplitude of 3% of the incident flux.

(6) Spatial Uniformity and Linearity of Detector Response

Figure 11:
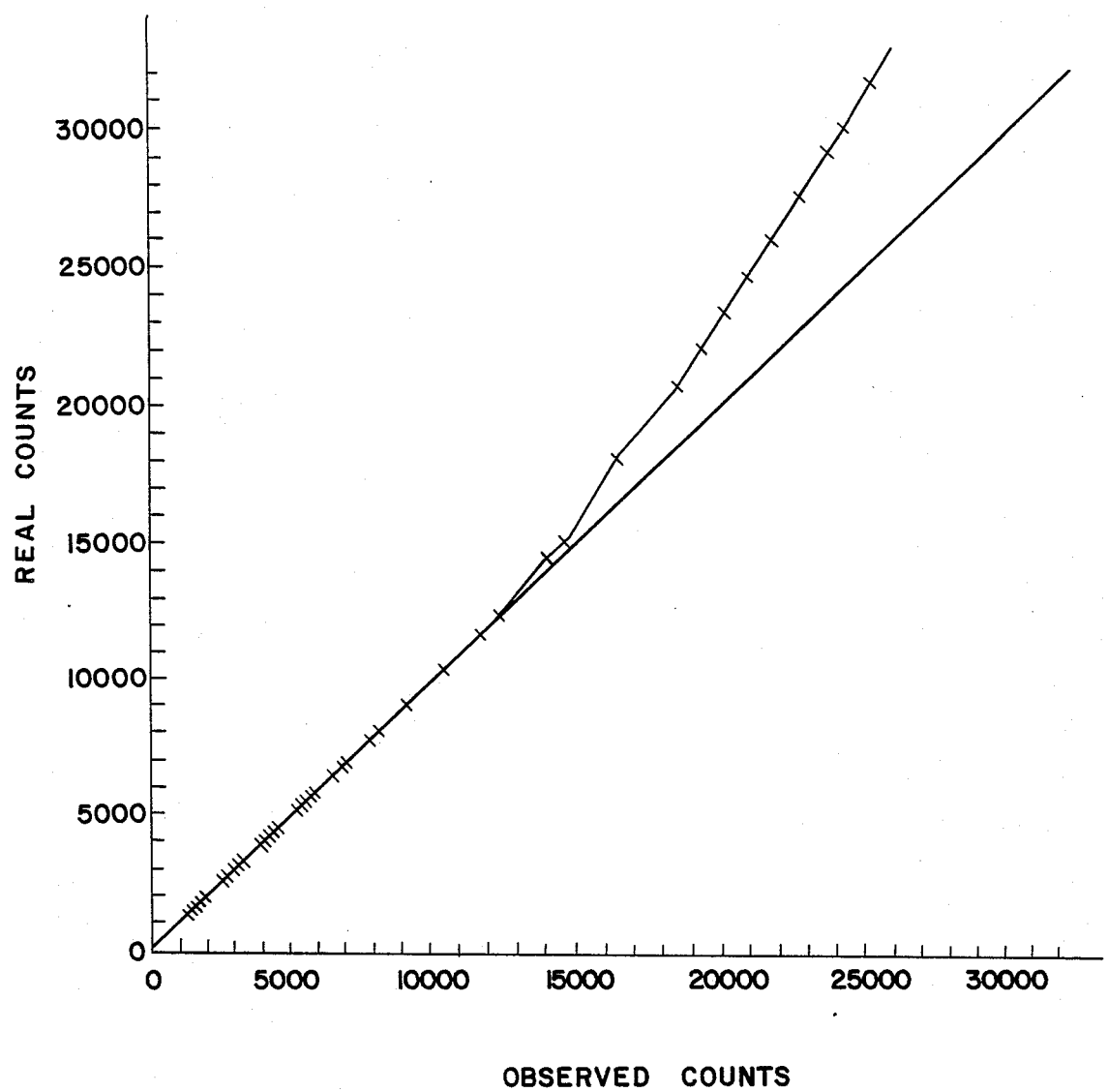
FIG. 11—Linearity of CCD based electro-optic detector response vs. incident intensity (30 x-rays=1 count).

Variations in the sensitivity of the detector were corrected using the procedure outlined in FIG. 9. One calibration frame was taken for every five measurements of transmitted intensity. This calibration measurement was used to correct each of the five transmitted intensity measurements. The map for zero offset and dark count effects was prerecorded along with a gain map. A linearity correction had to be applied to all of the data before the correction procedure shown in FIG. 9 was performed. FIG. 11 shows the measured linearity of the detector system before correction. Each "count" on the scale shown in FIG. 11 corresponds to 30 x-rays. It is seen that 300,000 x-rays per pixel can be recorded before a significant correction for linearity must be applied. Before the detector completely saturates, about $10^6$ x-rays/pixel can be recorded.

Figure 12:
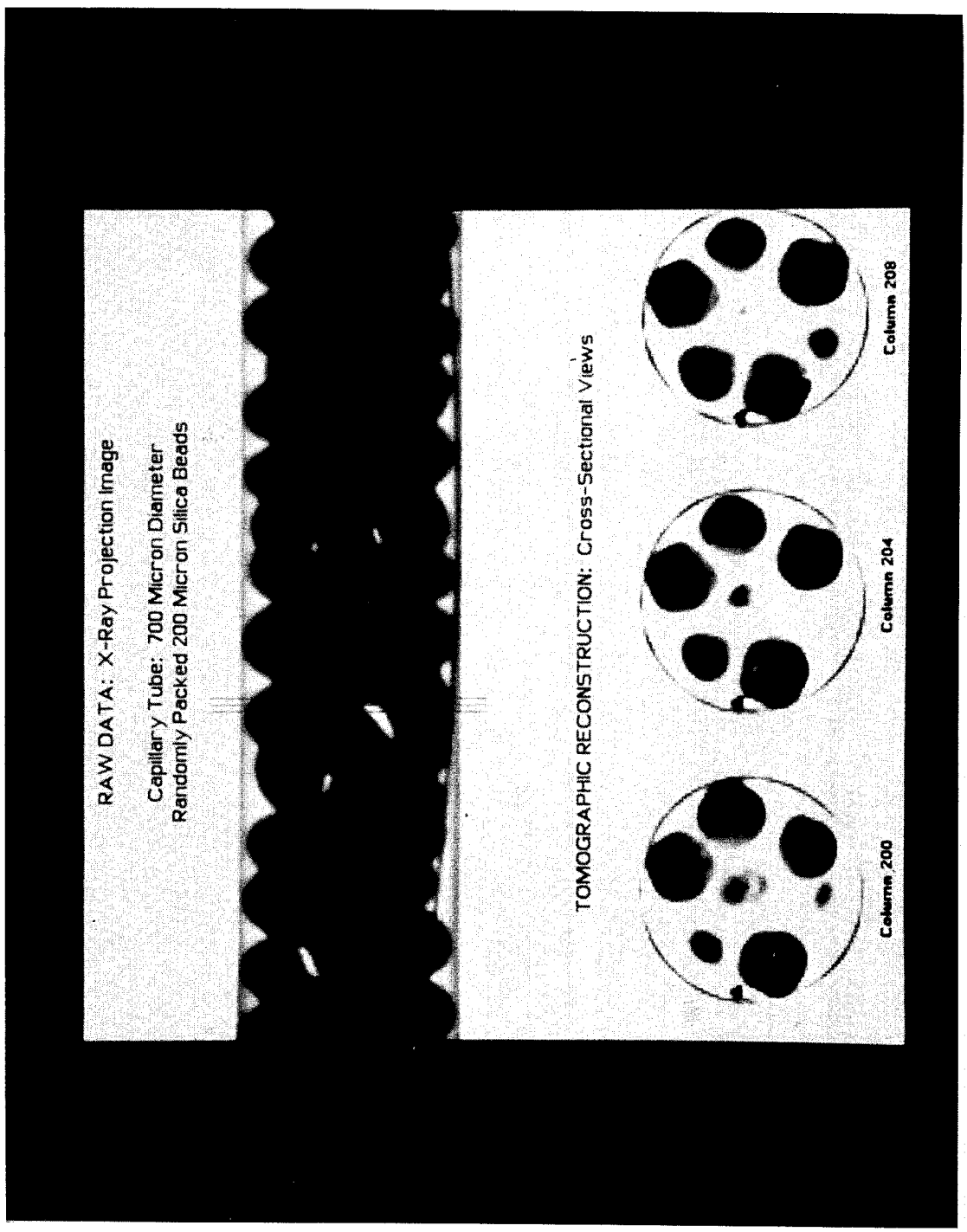
FIG. 12—Shown at the top of the figure is a single view ($I_p$) of a 750 m diameter glass capillary tube filled with 200 micron silica spheres and a single ten micron tungsten wire which runs along the tube length. Spatial resolution in the image ($I_p$) is approximately ten microns. At the bottom of the figure are cross sectional reconstructions of the tube at the positions indicated by the three lines drawn across the image on top. It is seen that the cross sections of the silica beads are plainly visible in the image. At the left edge of the tube cross section the small dark spot corresponds to the 10 micron turngsten wire.

Using the projection values calculated, the data was inverted using the DFI technique. FIG. 12 shows projection data acquired in one view of the hollow glass tube as well as reconstructed across sectional views at the points indicated in FIG. 12. It is seen that the 200 micron glass spheres are clearly visible in the cross-sectional images as well as the 10 micron tungsten wires. Spatial resolution achieved in this reconstruction is more than 25 times better than that achieved with conventional medical CAT scanners.

What is claimed is:

1. An apparatus for producing tomographic images of an object mounted with respect to a rotation axis, said object irradiated by a beam of plane parallel collimated x-ray radiation transmitted in a plurality of rays through a set of coplanar sections of said object as viewed from a plurality of angles about said rotation axis comprising:
   (a) an imaging two-dimensional electro-optic detector to simultaneously record the transmitted radiation from multiple stacked planes through said object irradiated by a beam of plane parallel collimated x-ray radiation wherein the electro-optic detector includes an energy converter, an electro-optic readout and a means for format alteration, said format alteration means being focused;
   (b) means to determine projection data from transmitted radiation with respect to one or more reference calibration exposures, wherein a projected image of said rotation axis is aligned on said readout, wherein said object is aligned with respect to said rotation axis, and wherein said electro-optic detector has a spatially uniform response and low signal dependent background;
   (c) means to determine a three-dimensional reconstructed image of attenuation coefficients of said object from said projection data.

2. The apparatus of claim 1 further comprising a means to correct the alignment of pixels of said two-dimensional electro-optic detector so that they can be assigned to a two-dimensional set of points in a plane parallel and orthogonal to said axis of rotation.

3. The apparatus of claim 1 further comprising a means to determine and assure the three-dimensional mechanical drift of the apparent position of said rotation axis projected on said two-dimensional electro-optic detector is reduced.

4. The apparatus of claim 1 wherein said apparatus is calibrated so as to reduce the intensity of ring artifacts appearing in the reconstructed three-dimensional image.

5. The apparatus of claim 4 wherein said means for reducing the intensity of ring artifacts reduces said ring artifacts to less than 10% of the local value of said reconstructed image.

6. The apparatus of claim 1 wherein said means for format alteration of said imaging two-dimensional electro-optic detector yields a spatial resolution, t, less than 5 pixels on the detector.

7. The apparatus of claim 6 further comprising a means for rotation axis alignment in three-dimensional space which corrects a projected displacement of any detected point along the rotation axis to less than 4t, where t is said spatial resolution.

8. The apparatus of claim 2 wherein said means to correct alignment for pixels is a mathematical transformation of transmitted radiation received by said two dimensional electro-optic detector.

9. The apparatus of claim 7 wherein said means for rotation axis alignment includes a three-dimensional adjustment in space of relative orientation of said object and said electro-optic detector.

10. The apparatus of claim 7 wherein said means for rotation axis alignment is a mathematical transformation of transmitted radiation received by said two dimensional electro-optic detector.

11. The apparatus of claim 7 wherein said means for rotation axis alignment corrects said alignment to within an angular accuracy of 2t/d, where d is the number of pixels across the maximum diameter of said object about the rotation axis, and t is said resolution in pixels.

12. The apparatus of claim 1 further comprising a means to calibrate and correct linearity of detector response over the useful dynamic range.

13. The apparatus of claim 1 wherein said imaging electro-optic detector includes a cellular energy conversion device.

14. The apparatus of claim 13 wherein said cellular energy conversion device includes means for translation.

15. The apparatus of claim 1 wherein said means to determine a reconstructed image of the attenuation coefficients includes a means for acquiring a calibration image and a means for processing said image to reduce scattered light effects.

16. The apparatus of claim 1 wherein said format alteration of said electro-optic detector such that the detector resolution is less than 2 pixels.

17. The apparatus of claim 1 further comprising a means for rotating either the source of radiation or the object about an axis.

18. The apparatus of claim 12 wherein said detector has a calibrated linearity such that the response versus incident intensity is better than 0.5% over the useful dynamic range.

19. The apparatus of claim 1 further including a source of radiation.

20. The apparatus of claim 1 further including a display device.

21. The apparatus of claim 1 wherein said electro-optic detector is focused to within a factor of 4 of the resolution obtained at best focus.

22. A method for producing tomographic images of an object comprising:
  (a) irradiating said object by a beam of plane parallel collimated x-ray radiation transmitted in a plurality of rays through a set of coplanar sections of said object as viewed from a plurality of angles about a rotation axis;
  (b) simultaneously recording said transmitted radiation from multiple stacked planes by a two-dimensional imaging electro-optic detector, wherein said electro-optic detector includes an energy converter and alters the image format, the format alteration being focused;
  (c) determining and aligning in three-dimensional space the projected position of said rotation axis on said electro-optic detector;
  (d) aligning said object in three-dimensional space with respect to said rotation axis;
  (e) determing and assuring spatial uniformity of detector response;
  (f) measuring and reducing signal dependent background;
  (g) determining projection data from the transmitted radiation with respect to one or more reference calibration exposures;
  (h) reconstructing an image of attenuation coefficients of said object from said projection data.

23. The method of claim 22 further comprising the step of correcting the alignment of pixels of said electro-optic detector so that they can be assigned to a planar set of points parallel and orthogonal to said axis of rotation.

24. The method of claim 22 further comprising the step of determining and assuring that the mechanical drift of the apparent position of said rotation axis projected on said electro-optic detector is reduced.

25. The method of claim 22 further comprising the step of correcting pixel to pixel variations and reducing the intensity of ring artifacts appearing in the reconstructed image.

26. The method of claim 22 wherein the step for determining and aligning said projected image of said rotation axis is performed so as to correct projected displacement of any detected point along the rotation axis to less than 4t, where t is said detector resolution to correct alignment of pixels relative positions of said object and said electro-optic detector.

27. The method of claim 23 wherein the step of alignment of pixels is a mathematical transformation of said transmitted radiation recorded by said electro-optic detector.

28. The method of claim 22 wherein said step for determining and aligning said projected position of said rotation axis step includes mechanical adjustment of relative orientation of said object and said electro-optic detector.

29. The method of claim 22 wherein said step for determining and aligning said projected position of said rotation axis is a mathematical transformation of said detected transmitted radiation.

30. The method of claim 22 wherein said step for determining and aligning said projected position of said rotation axis corrects said alignment to within an angular accuracy of 2t/d, where d is the number of pixels across the maximum diameter of said object about the rotation axis, and t is said resolution in pixels.

31. The method of claim 22 further comprising calibrating and correcting linearity of response of said detector over the useful dynamic range.

32. The method of claim 22 further comprising the step of translating said energy converter.

33. The method of claim 22 wherein said step of determining said projected data includes processing said image to reduce scattered light effects.

34. The method of claim 22 further comprising the step of focusing said electro-optic detector such that the detector resolution is less than 2 pixels.

35. The method of claim 22 further comprising the step of rotating either the source of radiation or the object about an axis.

36. The method of claim 31 wherein said calibrating step is performed such that the linearity of response versus incident intensity of said detector is better than 0.5% over the useful dynamic range.

37. The method of claim 22 further comprising the step of displaying the image of attenuation coefficients of said object obtained in the reconstruction step.

38. The method of claim 22 further comprising the step of focusing the electro-optic detector to within a factor of 4 of the resolution obtained at best focus.

* * * * *